(12) United States Patent
Tse-Dinh et al.

(10) Patent No.: US 10,266,550 B2
(45) Date of Patent: Apr. 23, 2019

(54) BACTERIAL TOPOISOMERASE I INHIBITORS WITH ANTIBACTERIAL ACTIVITY

(71) Applicants: The Florida International University Board of Trustees, Miami, FL (US); University of Hawaii, Honolulu, HI (US)

(72) Inventors: Yuk-Ching Tse-Dinh, Coral Gables, FL (US); Dianqing Sun, Hilo, HI (US)

(73) Assignees: THE FLORIDA INTERNATIONAL UNIVERSITY BOARD OF TRUSTEES, Miami, FL (US); UNIVERSITY OF HAWAII, Honolulu, HI (US)

( * ) Notice: Subject to any disclaimer, the term of this patent is extended or adjusted under 35 U.S.C. 154(b) by 0 days.

(21) Appl. No.: 15/707,537

(22) Filed: Sep. 18, 2017

(65) Prior Publication Data
US 2018/0079757 A1 Mar. 22, 2018

Related U.S. Application Data

(60) Provisional application No. 62/395,652, filed on Sep. 16, 2016.

(51) Int. Cl.
| | | |
|---|---|---|
| C07D 498/04 | (2006.01) | |
| A61K 31/538 | (2006.01) | |
| C07D 498/06 | (2006.01) | |

(52) U.S. Cl.
CPC .......... *C07D 498/04* (2013.01); *A61K 31/538* (2013.01); *C07D 498/06* (2013.01)

(58) Field of Classification Search
CPC ... C07D 498/04; A61K 31/536; A61K 31/538
See application file for complete search history.

(56) References Cited

PUBLICATIONS

RADL, 1989, Collect. Czech. Chem. Commun. vol. 54, p. 506-515. (Year: 1989).*
Ahmed, W. et al., "Conditional silencing of topoisomerase I gene of *Mycobacterium tuberculosis* validates its essentiality for cell survival." FEMS Microbiol. Lett., 2014, 353: 116-123.
Aldred, K. J. et al., "Mechanism of Quinolone Action and Resistance." Biochemistry, 2014, 53: 1565-1574.
Andrews, J. M., "Determination of minimum inhibitory concentrations." Journal of Antimicrobial Chemotherapy, 2001, 48: Suppl. S1: 5-16.
Bansal, S. et al., "3,4-Dimethoxyphenyl bis-benzimidazole, a novel DNA topoisomerase inhibitor that preferentially targets *Escherichia coli* topoisomerase I." J. Antimicrob. Chemother., 2012, 67: 2882-2891.
Braun, M., Silhavy, T. J., "ImpOstA is required for cell envelope biogenesis in *Escherichia coli*." Molecular Microbiology, 2002, 45 (5): 1289-1302.
Chen, S. H. et al., "New mechanistic and functional insights into DNA topoisomerases." Annu. Rev. Biochem., 2013, 82: abstract.
Cheng, B. et al., "Compounds with antibacterial activity that enhance DNA cleavage by bacterial DNA topoisomerase I." Journal of Antimicrobial Chemotherapy, 2007, 59: 640-645.
Chu, D. T. W., Maleczka Jr., R. E., "Synthesis of 4-oxo-4 H-quino[2,3,4-i,j][1,4]-benoxazine-5-carboxylic acid derivatives." Journal of Heterocyclic Chemistry, Mar. 1987, 24 (2): Abstract.
Cramer, R. D. III et al., "Comparative Molecular Field Analysis (CoMFA). 1. Effect of Shape on Binding of Steroids to Carrer Proteins." J. Am. Chem. Soc., 1988, 110: 5959-5967.
Dinardo, S. et al., "*Escherichia coli* DNA topoisomerase I mutants have compensatory mutations in DNA gyrase genes." Cell, Nov. 1982, 31 (1): abstract.
Drlica, K, "Control of bacterial DNA supercoiling." Molecular Microbiology, 1992, 6 (4): 425-433.
Drlica, K, Malik, M., "Fluoroquinolones: Action and Resistance." Current Topics in Medicinal Chemistry, 2003, 3: 249-282.
Duan, W. et al., "Design and Synthesis of Fluoroquinophenoxazines That Interact with Human Telomeric G-Quadruplexes and Their Biological Effects." Molecular Cancer Therapeutics, Dec. 2001, 1: 103-120.
Engström, A., "Fighting an old disease with modern tools: characteristics and molecular detection methods of drug-resistant *Mycobacterium tuberculosis*." Infect. Dis. (Lond), 2016, 48 (1): abstract.
Falzari, K. et al., "In Vitro and In Vivo Activities of Macrolide Derivatives against *Mycobacterium tuberculosis*." Antimicrobial Agents and Chemotherapy, Apr. 2005, 49 (4): 1447-1454.
Fan, J. Y. et al., "Self-assemby of a quinobenzoxazine-Mg2+ complex on DNA: a new paradigm for the structure of a drug-DNA complex and implications for the structure of the quinolone bacterial gyrase-DNA complex." J. Med. Chem., Feb. 1995, 38 (3): abstract.
Friedman, N. D. et al., "The negative impact of antibiotic resistance." Clin. Microbiol. Infect., 2016, 22: 416-422.
G6G Directory of Omics and Intelligent Software, "SYBYL-X Suite." [retrieved on Nov. 15, 2017] Retrieved from the Internet:< URL:http://gbg-50Hwaredirectory.com/bio/proteomics/structure-modeling/20710-Tripos-SYBYL-X-Suite.php>.
Garcia, M. T. et al., "New Alkaloid Antibiotics That Target the DNA Topoisomerase I of *Streptococcus pneumoniae*." Journal of Biological Chemistry, Feb. 2011, 286 (8): 6402-6413.
Godbole, A. A. et al., "Inhibition of *Mycobacterium tuberculosis* topoisomerase I by m-AMSA, a eukaryotic type II topoisomerase poison." Biochemical and Biophysical Research Communications, 2014, 446: 916-920.

(Continued)

*Primary Examiner* — Rebecca L Anderson
*Assistant Examiner* — Karen Cheng
(74) *Attorney, Agent, or Firm* — Saliwanchik, Lloyd & Eisenschenk

(57) ABSTRACT

The present invention provides compounds as bacterial topoisomerase inhibitors with antibacterial activity. The present invention also provides pharmaceutical compositions comprising at least one of the compounds and methods of using the compounds and pharmaceutical compositions as antibacterial agents for treating infectious diseases.

15 Claims, 5 Drawing Sheets

(56) References Cited

PUBLICATIONS

Hallett, P. et al., "Cloning of the DNA gyrase genes under tac promoter control: overproduction of the gyrase A and B proteins." Gene, Sep. 1990, 93 (1): abstract.
Kang, D. H. et al., "New insight for fluoroquinophenoxazine derivatives as possibly new potent topoisomerase inhibitor." Bioorg Med Chem Lett, Feb. 2008, 18 (4): abstract.
Masand, V.H. et al., "Optimization of antiproliferative activity of substituted phenyl 4-(2-oxoimidazolidin-a-yl) benzenesulfonates: QSAR and CoMFA analyses." Eur J Pharm Sci, Sep. 2015, 77: abstract.
Massé, E., Drolet, M., "Relaxation of Transcription-induced Negative Supercoiling Is an Essential Function of *Escherichia coli* DNA topoisomerase I." The Journal of Biological Chemistry, Jun. 1999, 274 (23): 16654-16658.
Matteelli, A. et al., "Extensively drug-resistant tuberculosis: epidemiology and management." Clinical Epidemiology, Apr. 2014, 6: 111-118.
Narula, G. et al., "The Strictly Conserved Arg-321 Residue in the Active Site of *Escherichia coli* Topoisomerase I Plays a Critical Role in DNA Rejoining." Journal of Biological Chemistry, May 2011, 286 (21): 18673-18680.
Nimesh, H. et al., "Synthesis and Biological Evaluation of Novel Bisbenzimidazoles as *Escherichia coli* Topoisomerase IA Inhibitors and Potential Antibacterial Agents." Journal of Medicinal Chemistry, May 2014, 1-73.
Permana, P. A. et al., "Quinobenoxazines: a class of novel antitumor quinolones and potent mammalian DNA topoisomerase II catalytic inhibitors." Biochemistry, Sep. 1994, 33 (37): abstract.
Podlogar, B. L. et al., "Synthesis and evaluation of 4-(N,N-diarylamino)piperidines with high selectivity to the delta-opioid receptor: a combined 3D-QSAR and ligand docking study." Drug Des Discov, 2000, 17 (1): abstract.
Pruss, G. J. et al., "*Escherichia coli* DNA topoisomerase I mutants: increased supercoiling is corrected by mutations near gyrase genes." Cell, Nov. 1982, 31 (1): abstract.
Rádl, S., Zikán, V., "Synthesis and Antimicrobial Activity of Some 3-oxo-3H-Pyrido[3,2,1-kl]Phenoxazine-2-carboxylic Acids." Collect. Czech. Cham. Commun., 1989, 54: 506-515.
Ravishankar, S. et al., "Genetic and chemical validation identifies *Mycobacterium tuberculosis* topoisomerase I as an attractive antitubercular target." Tuberculosis, Sep. 2015, 95 (5): abstract.
Sampson, B. A. et al., "Identification and Characterization of a New Gene of *Escherichia coli* K-12 Involved in Outer Membrane Permeability." Genetics, Jul. 1989, 122: 491-501.
Schoeffler, A. J., Berger, J. M., "DNA topoisomerases: harnessing and constraining energy to govern chromosome topology." Q. Rev. Biophys., Feb. 2008, 41 (1): abstract.
Ståhle, L., Wold, S., "Partial least squares analysis with cross-validation for the two-class problem: A Monte Carlo study." Journal of Chemometrics, Jul. 1987, 1 (3): abstract.
Suerbaum, S. et al., "Topoisomerase I of Helicobacter pylori: juxtaposition with a flagellin gene (flaB) and functional requirement of a fourth zinc ringer motif." Gene, Mar. 1998, 210 (1): abstract.
Tan, K. et al., "Structural basis for suppression of hypernegative DNA supercoiling by *E. coli* topoisomerase I." Nucleic Acids Research, 2015, 43 (22): 11031-11046.
Tang, S. C., Shapiro, T. A., "Newly Identified Antibacterial Compounds Are Topoisomerase Poisons in African Trypanosomes." Antimicrobial Agents and Chemotherapy, Feb. 2010, 54 (2): 620-626.
Tomašić, T., Mašič, L. P., "Prospects for Developing New Antibacterials Targeting Bacterial Type IIA Topoisomerases." Current Topics in Medicinal Chemistry, 2014, 14: 130-151.
Tse-Dinh, Y., "Survey and Summary: Bacterial topoisomerase I as a target for dicovery of antibacterial compounds." Nucleic Acids Research, 2009, 37 (3): 731-737.
Tse-Dinh, Y., "Targeting bacterial topoisomerase I to meet the challenge of finding new antibiotics." Future Med. Chem., Mar. 2015, 7 (4): 459-471.
Vos, S. M. et al., "All tangled up: how cells direct, manage and exploit topoisomerase function." Nat. Rev. Mol. Cell. Biol., Mar. 2015, 12 (12): 827-841.
Yamaguchi, Y., Inouye, M., "An endogenous protein inhibitor, YjhX (TopAI), for topoisomerase I from *Escherichia coli*." Nucleic Acids Research, 2015, 43 (21): 10387-10396.
Yigit, H., Reznikoff, W. S., "*Escherichia coli* DNA Topoisomerase I Copurifies with Tn5 Transposase, and Tn5 Transposase Inhibits Topoisomerase I." Journal of Bacteriology, May 1999, 181 (10): 3185-3192.
Yigit, H., Reznikoff, W. S., "*Escherichia coli* DNA Topoisomerase I and Suppression of Killing by Tn5 Transposase Overproduction: Topoisomerase I Modulates Tn5 Transposition." Journal of Bacteriology, Nov. 1998, 181 (22): 5866-5874.
Yu, X. et al., "Synthesis, evaluation, and CoMFA study of fluoroquinophenoxazine derivatives as bacterial topoisomerase IA inhibitors." European Journal of Medicinal Chemistry, 2017, 125: 515-527.
Zhang, Z. et al., "Crystal structure of a covalent intermediate in DNA cleavage and rejoining by *Escherichia coli* DNA topoisomerase I." PNAS, Apr. 2011, 108 (17): 6939-6944.

\* cited by examiner

BACTERIAL TOPOISOMERASE I INHIBITORS WITH ANTIBACTERIAL ACTIVITY

CROSS-REFERENCE TO RELATED APPLICATIONS

This application claims the priority benefit of U.S. Provisional Application Ser. No. 62/395,652, filed Sep. 16, 2016, which is incorporated herein by reference in their entireties.

GOVERNMENT SUPPORT

This invention was made with government support under AI069313, GM103466 and AI092315 awarded by the National Institutes of Health. The government has certain rights in the invention.

BACKGROUND OF INVENTION

Microbial pathogens are becoming increasingly resistant to current antibiotics, limiting the availability of clinical treatment options for bacterial infections (1). It is imperative to develop novel classes of antibacterial compounds, preferably against a new target, to avoid cross-resistance. *Tuberculosis* (TB) infects 9.6 million people a year and causes 1.5 million deaths each year (2). The problem presented by multi-drug resistance is illustrated by the 480,000 cases of multi-drug resistant TB (MDR-TB) that do not respond to first line treatment drugs, with around ten percent of these cases being extensively-drug resistant *tuberculosis* (XDR-TB) that are resistant to even some of the second line drugs (2, 3). New combinations of anti-TB drugs are needed to treat the MDR-TB and XDR-TB cases.

Topoisomerases are needed in every organism to regulate DNA topology so that vital cellular processes including DNA replication, transcription, recombination and repair can proceed without hindrance (4, 5). Type IIA topoisomerases cut and rejoin a double strand of DNA during catalysis (6). DNA gyrase and topoisomerase IV are prokaryotic type IIA topoisomerases that have been extensively explored as validated targets for antibacterial therapy in the clinic (7, 8). At least one type IA topoisomerase is present in every bacterial pathogen to resolve topological barriers that require the cutting and rejoining of a single strand of DNA and passage of DNA through the transient break (9). Topoisomerase I is the major type IA topoisomerase activity responsible for preventing excessive negative supercoiling in bacteria (10, 11).

Bacterial topoisomerase has received some recent interest as a novel antibacterial drug target (9, 12). Poison inhibitors of topoisomerase enzymes can lead to the accumulation of the intermediate topoisomerase-DNA cleavage complex and subsequently result in bacterial or cancer cell death. *Escherichia coli* topoisomerase I (EcTopI) is the most extensively studied type IA topoisomerase, with crystal structures of covalent cleavage complex (13) and full-length enzyme-DNA complex (14) available. Inhibition of EcTopI by endogenous polypeptide inhibitors (15-17) can lead to cell killing even though compensatory mutations could allow *E. coli* strains with topA deletion to be viable (18, 19). There is also evidence that topoisomerase I function is essential for a number of bacterial pathogens including *Streptococcus pneumoniae* (20) and *Helicobacter pylori* (21). There is only one type IA topoisomerase encoded by the genomes of Mycobacteria. *Mycobacterium tuberculosis* topoisomerase I (MtbTop1) has been demonstrated in genetic studies to be essential for viability both in vitro (22, 23) and in vivo (23). Experimental data showed that the minimal inhibitory concentrations (MICs) of select small molecules against *Mycobacterium tuberculosis* can be shifted by overexpression of topoisomerase I (23, 24), further validating topoisomerase I as a vulnerable target in *M. tuberculosis* for chemical inhibition.

Clinically, topoisomerase enzymes represent attractive and successful targets for anticancer and antibacterial chemotherapy. Many of the small molecules identified previously as bacterial topoisomerase I inhibitors are DNA intercalators (20, 24-26) or minor groove binders (27, 28) that would not be attractive candidates for antibiotics development. Therefore, there is an urgent need to develop compounds that target bacterial pathogens, in particular, through the inhibition of bacterial topoisomerase I.

BRIEF SUMMARY

The current invention provides compounds and methods for inhibiting the activity of topoisomerase. These compounds and methods according to the current invention can further be used to control bacterial pathogens. The current invention also provides pharmaceutical compositions comprising one or more compounds of the current invention, and methods comprising administration of the compositions for treating a surface or a subject infected with a bacterial pathogen.

In one embodiment, the compound comprises a scaffold having a general structure of (I):

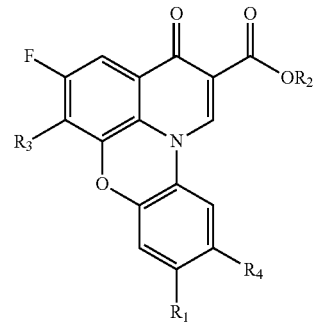

(I)

wherein $R_1$, $R_2$, $R_3$ and $R_4$ are each independent groups, wherein $R_1$, $R_3$ and $R_4$ are each independently selected from H, —OH, —$NH_2$, —$NO_2$, —NHMe, acetyl group (—Ac), —CN, —NHAc, —$NHCH_2CH_2NH_2$, —$CF_3$, fluorine, chloride, bromine, iodine, alkyl, substituted alkyl, aryl, substituted aryl, heteroaryl, substituted heteroaryl, cycloalkyl, substituted cycloalkyl, cycloalkenyl, substituted cycloalkenyl, heterocycloalkyl, substituted heterocycloalkyl, amino group, and substituted amino group; and $R_2$ is selected from H, alkyl, substituted alkyl, aryl, substituted aryl, heteroaryl, substituted heteroaryl, cycloalkyl, substituted cycloalkyl, cycloalkenyl, and substituted cycloalkenyl.

In a further embodiment, $R_1$ is selected from $NH_2$, —$NO_2$, —Ac, —CN, —NHAc and —$CF_3$; $R_2$ is H or an ethyl group; $R_3$ is an amino group, substituted amino group including amine group with lipophilic side chainsor selected from:

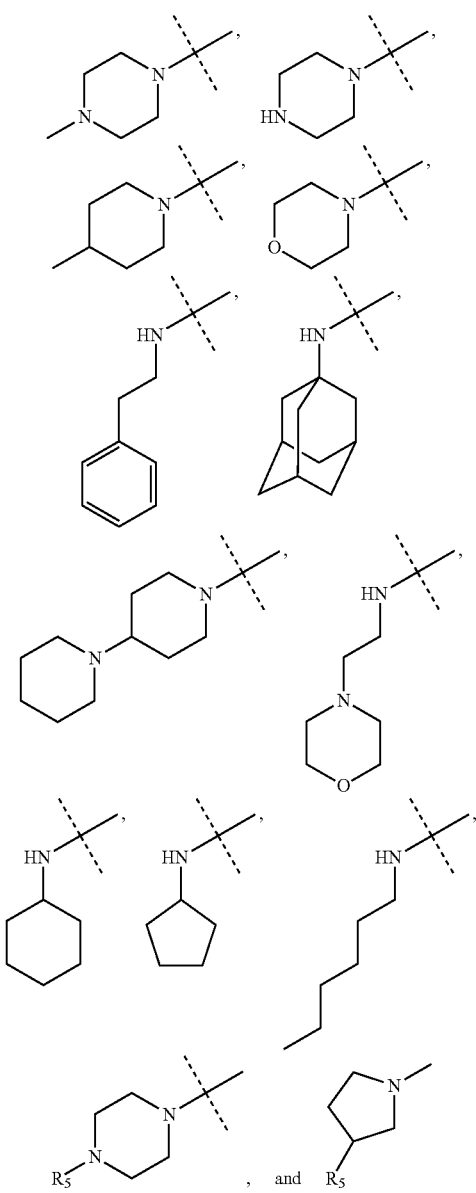

wherein $R_5$ is H, OH, Me, $NH_2$, $NO_2$, tert-butyloxycarbonyl (Boc) amine (e.g., NHBoc), fluorine, chloride, bromine, iodine, alkyl, or substituted alkyl.

In one embodiment, the compounds have activity against bacterial pathogens, including both gram-positive and negative bacteria. In a further embodiment, the compounds have activity against mycobacteria. In another further embodiment, the compounds have activity against *E. coli, Staphylococcus aureus, Streptococcus pneumoniae, Helicobacter pylori, Mycobacterium bovis, Mycobacterium africanum, Mycobacterium microti, Mycobacterium canetti, Mycobacterium smegmatis* and/or *Mycobacterium tuberculosis*. In a preferred embodiment, the compounds have activity against *M. tuberculosis*.

In other embodiments, the compounds have activity against non-*tuberculosis* mycobacteria (NTM), e.g., *Mycobacterium avium* complex (MAC), *Mycobacterium kansasii*, and *Mycobacterium abscessus*, and thus, can be used to treat NTM infection in a subject. NTM are all the other mycobacteria which can cause pulmonary disease. NTM can also infect skin, soft tissues and lungs of cystic fibrosis patients.

In one embodiment, the compounds are used for treatment of infections in the form of biofilms formed by mycobacteria, including TB and NTM. Such biofilms are often difficult to treat with antibiotics.

In another embodiment, the compounds have activity against drug resistant bacterial pathogens, preferably, *M. tuberculosis* and *Staphylococcus aureus*, more preferably, Methicillin-resistant *Staphylococcus aureus* (MRSA).

In one embodiment, the compounds inhibit the activity of topoisomerase, preferably, the type IA family of topoisomerase, more preferably, bacterial topoisomerase I, Additionally, the compounds exhibit selective inhibition of bacterial topoisomerase I over DNA gyrase.

In one embodiment, the compounds target bacterial pathogens through the inhibition of topoisomerase. In a further embodiment, the compounds inhibit the growth of bacterial pathogens by targeting the type IA family of topoisomerase. In a preferred embodiment, the compounds exhibit cytotoxicity by inhibiting bacterial topoisomerase I. In a more preferred embodiment, the compounds inhibit *M. tuberculosis* topoisomerase I (MtbTopI).

In one embodiment, the compounds are bactericidal against bacterial pathogens, including both gram-positive and negative bacteria. In a further embodiment, the compounds are bactericidal against mycobacteria. In another further embodiment, the compounds are bactericidal against *E. coli, Staphylococcus aureus, Streptococcus pneumoniae, Helicobacter pylori, M smegmatis* and/or *M. tuberculosis*, preferably, *M. tuberculosis*.

In another embodiment, the compounds are bactericidal against drug resistant bacterial pathogens, preferably, *M. tuberculosis* and *Staphylococcus aureus*, more preferably, Methicillin-resistant *Staphylococcus aureus* (MRSA).

In one embodiment, the compounds are used as antibacterial drugs in antibacterial therapy. In a specific embodiment, the compounds are used in treatment of infectious diseases, preferably, *tuberculosis*.

In one embodiment, the compounds can be used as antituberculosis agents.

In one embodiment, the current invention provides a pharmaceutical composition comprising one or more compounds of the subject invention. The composition can further comprise a pharmaceutically acceptable carrier.

In a further embodiment, the compounds are in a pharmaceutically acceptable salt form or a form of free base. The composition may further contain pharmaceutically acceptable ingredients including metal salts and/or buffers. In certain embodiments, the pharmaceutical compositions can also include additional pharmaceutically active compounds know in the art.

In one embodiment, the current invention provides a pharmaceutical composition for treating conditions involving bacterial infection, preferably *tuberculosis*.

In one embodiment, the current invention also provides a method comprising the administration of an effective amount of the pharmaceutical composition for treating a subject infected with a bacterial pathogen. In a preferred embodiment, the subject is a human. In another preferred embodiment, the human patient is infected with *M. tuberculosis* and/or MRSA.

In one embodiment, the current invention provides a method for treating *Tuberculosis*, preferably, drug resistant *tuberculosis*.

The pharmaceutical composition can be administered through, for example, oral, rectal, bronchial, nasal, topical, buccal, sub-lingual, transdermal, vaginal, intramuscular, intraperitoneal, intravenous, intra-arterial, intracerebral, and interaocular administration.

The present invention also provides a method of inhibiting type IA topoisomerase in a subject, preferably in a human or a bacterium, comprising the administration of one or more of the compounds to the human or bacterium.

The present invention also provides a kit comprising the compounds or pharmaceutical compositions as described herein.

The compounds, compositions, methods and kits described herein can be used in connection with pharmaceutical, medical, veterinary, and disinfection applications, as well as fundamental biological research and methodologies, as would be identified by a skilled person upon reading the present disclosure.

DETAILED DISCLOSURE

Figure 1:
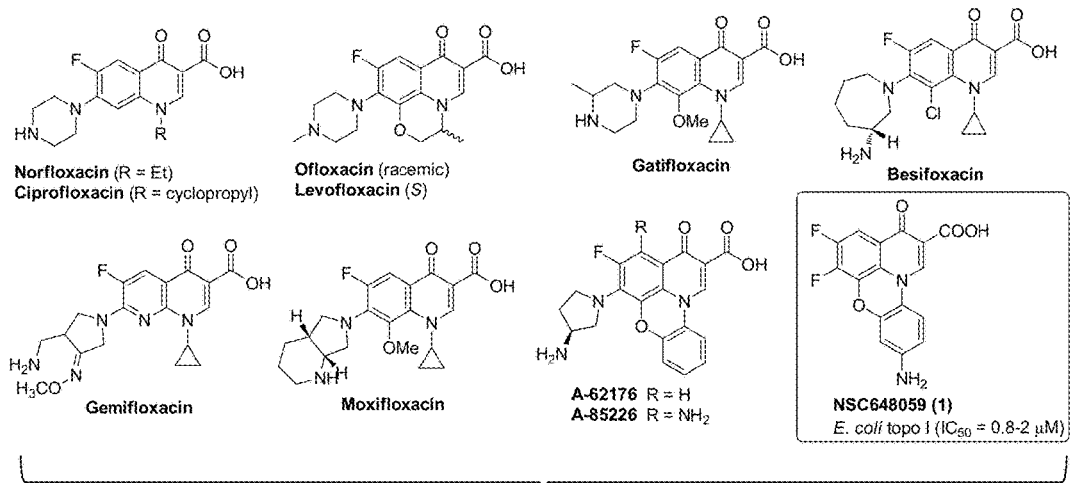
FIG. 1. Chemical structures of clinical fluoroquinolone antibiotics and fluoroquinophenzoxazine derivatives including topo I inhibitor 1.

The current invention provides compounds and methods for inhibiting the activity of topoisomerase. The compounds according to the invention have activity against one or more bacterial pathogens. The current invention also provides a pharmaceutical composition comprising at least one of the compounds, and methods comprising administration of the compositions for treating a subject infected with a bacterial pathogen or in need of such administration for inhibiting the activity of topoisomerase.

In one embodiment, the compound comprises a scaffold having a general structure of (I):

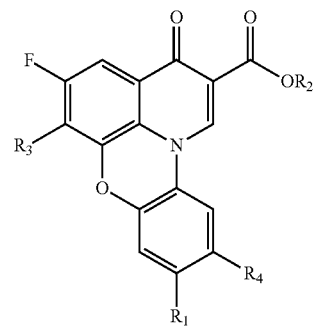

wherein $R_1$, $R_2$, $R_3$ and $R_4$ are each independent groups, wherein $R_1$, $R_3$ and $R_4$ are each independently selected from H, —OH, $NH_2$, —$NO_2$, —NHMe, —Ac, —CN, —NHAc, —$NHCH_2CH_2NH_2$, —$CF_3$, fluorine, chloride, bromine, iodine, alkyl, substituted alkyl, aryl, substituted aryl, heteroaryl, substituted heteroaryl, cycloalkyl, substituted cycloalkyl, cycloalkenyl, substituted cycloalkenyl, heterocycloalkyl, substituted heterocycloalkyl, amino group, and substituted amino group; $R_2$ is selected from H, alkyl, substituted alkyl, aryl, substituted aryl, heteroaryl, substituted heteroaryl, cycloalkyl, substituted cycloalkyl, cycloalkenyl, and substituted cycloalkenyl.

In another embodiment, $R_1$, $R_2$, $R_3$ and $R_4$ are each independent groups, wherein $R_1$ is selected from H, —OH, $NH_2$, —$NO_2$, —NHMe, —Ac, —CN, —NHAc, —$NHCH_2CH_2NH_2$, and —$CF_3$, $R_2$ is an H or an alkyl group; and $R_3$ is selected from fluorine, alkyl, substituted alkyl, aryl, substituted aryl, heteroaryl, substituted heteroaryl, cycloalkyl, substituted cycloalkyl, cycloalkenyl, substituted cycloalkenyl, heterocycloalkyl, substituted heterocycloalkyl, amino group, and substituted amino group with different functionalities such as piperazine, 1-methylpiperazine, and morpholine; and $R_4$ is selected from H, —OH, $NH_2$, —$NO_2$, —Ac, —CN, —NHAc, —$NHCH_2CH_2NH_2$, —$CF_3$, fluorine, chloride, bromine, iodine, and alkyl.

In a further embodiment, $R_1$ selected from $NH_2$, —$NO_2$, —Ac, —CN, and —$CF_3$.

In one embodiment, each R group may comprise other functional groups including quinolones, indoles, benzofurans, benzothiophenes, and biphenyls.

In a specific embodiment, each of the R groups may comprise a positively charged functional group, or a large aromatic group. Furthermore, each of the R groups may comprise a methyl naphthyl group wherein the naphthyl group includes but is not limited to dihydroxyphenyl, halogenated phenyls, aliphatic groups.

In one embodiment, the R groups may each independently include alkyl amines with varying chain lengths, cyclic amines (e.g., piperazine such as 1-methylpiperazine, morpholine, piperidine), cyclic alkyls, and aryl groups.

In a further embodiment, $R_2$ is H or an ethyl group. $R_3$ is an amino group, substituted amino group including amine group with lipophilic side chains or is selected from:

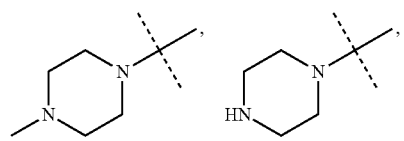

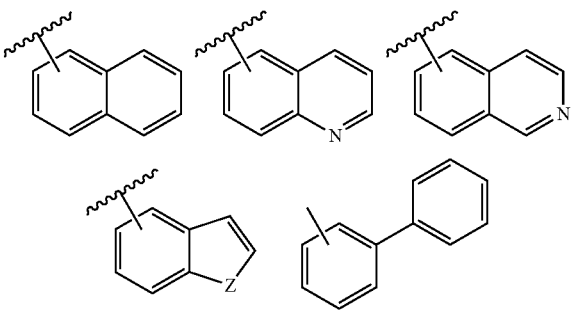

and wherein Z is preferably O, NH, NMe, or S.

In one embodiment, the compound is:

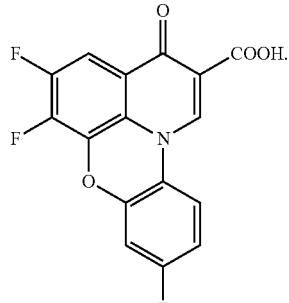

(1)

NSC648059

In one embodiment, the compound is selected from:

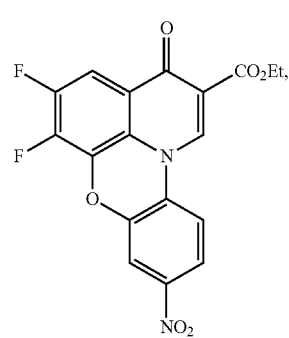

6a

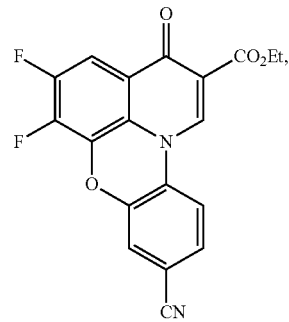

6b

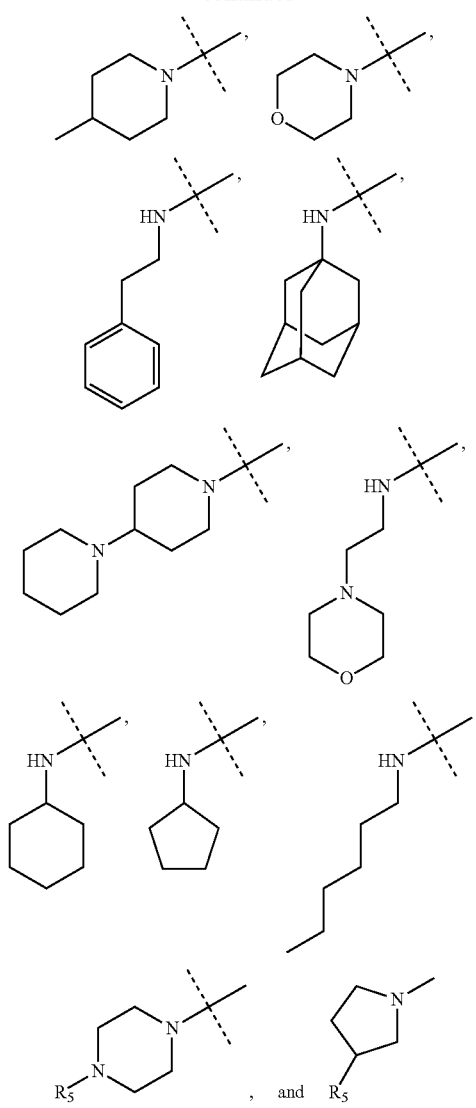

wherein R$_5$ is —H, —OH, -Me, —NH$_2$, —NO$_2$, —NHBoc, —Ac, —CN, —NHAc, —NHCH$_2$CH$_2$NH$_2$, —CF$_3$, fluorine, chloride, bromine, iodine, alkyl, or substituted alkyl.

In certain embodiments, each of R$_1$, R$_2$, R$_3$ and R$_4$ is selected from:

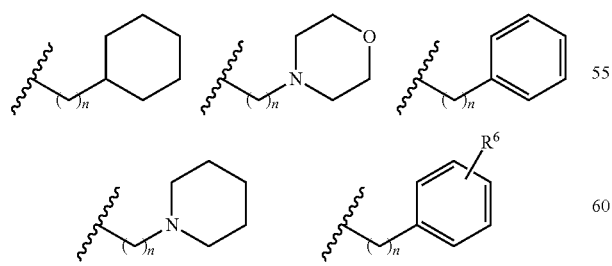

wherein n is at least 2, preferably ranging from 2 to 5.

In certain embodiments, each of R$_1$, R$_2$, R$_3$ and R$_4$ is independently selected from:

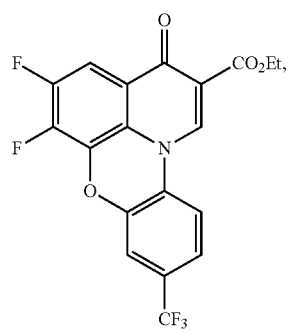
6c
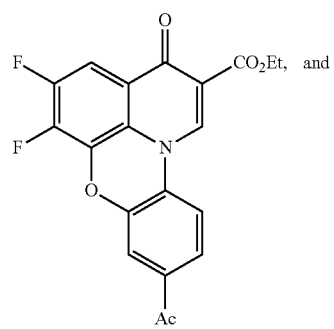
6d
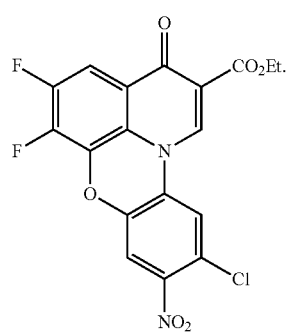
6e
In one embodiment, the compound is selected from:
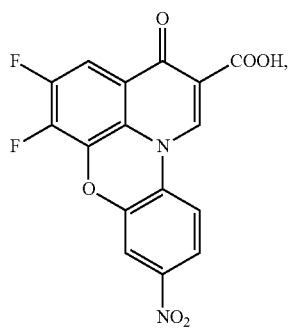
7a
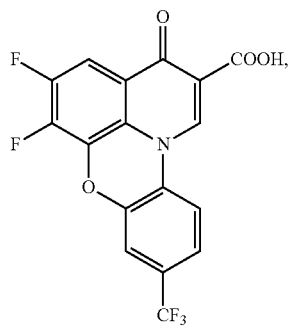
7b
7c
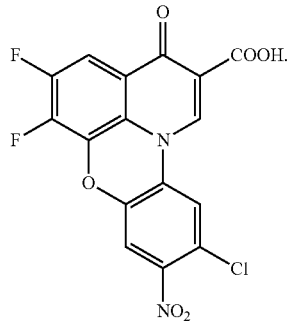
7d
7e In one embodiment, the compound is selected from:
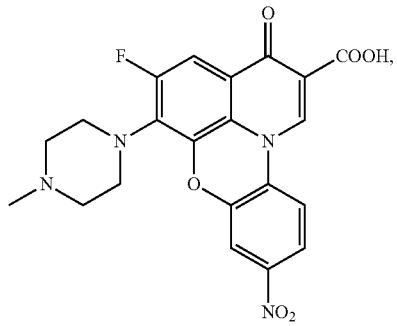
9
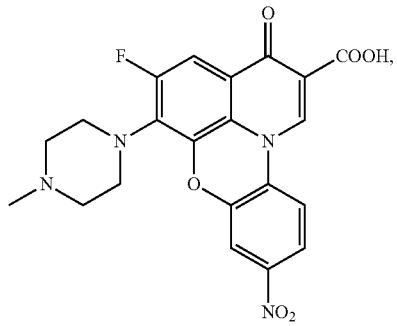
10a and
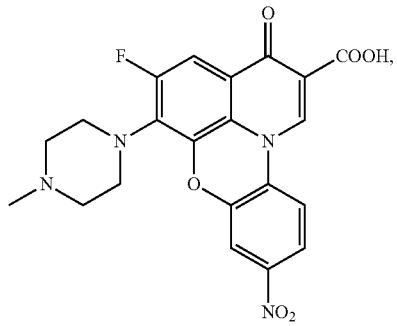
10b
In one embodiment, the compound is:
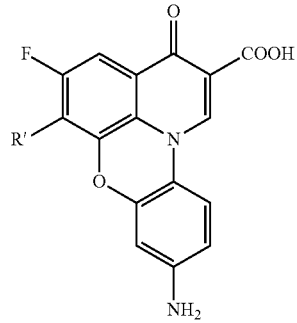
11
wherein R is selected from:
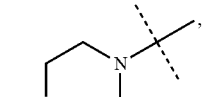
11a
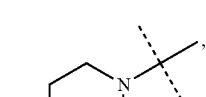
11b
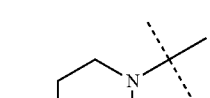
11c
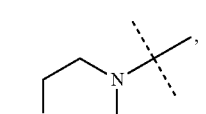
11d
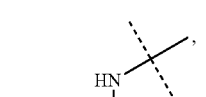
11e
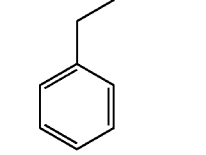
11f
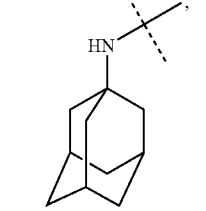
11g
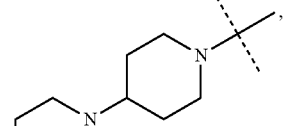
11h 11i

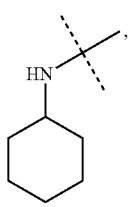

11j

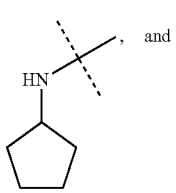, and

11k

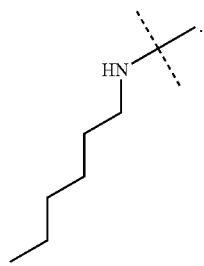.

In one embodiment, the compound is selected from:

12

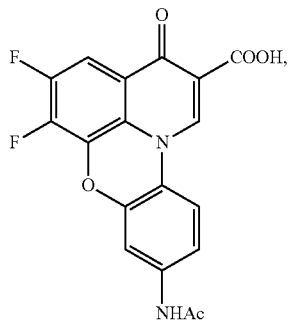

14

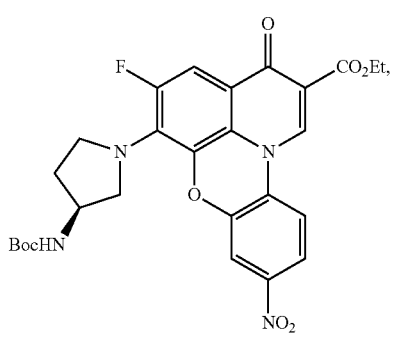

15

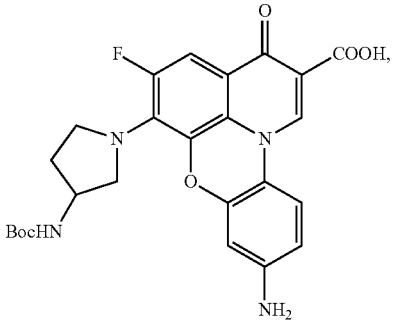

16

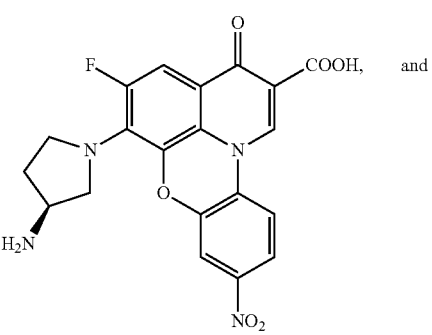

and

17

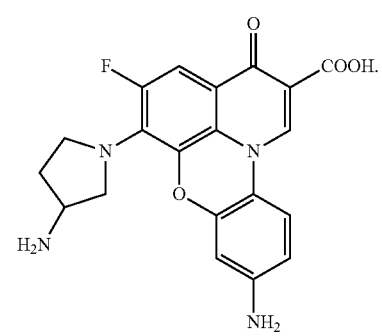.

In one embodiment, the compounds are fluoroquinophenzoxazine and derivatives thereof.

In one embodiment, certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein also are meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Chemical Definitions

The terms substituted, whether preceded by the term "optionally" or not, and substituent, as used herein, refer to the ability to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as an alkyl group, which is further substituted, for example, with fluorine at one or more positions).

Where a group may be substituted by one or more of a number of substituents, such substitutions are selected so as to comply with principles of chemical bonding and to give compounds that are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_3$, —$CH_2$—$CH_2$—N($CH_3$)—$CH_3$, —$CH_2$—S—$CH_2$—$CH_3$, —CH—$CH_{25}$—S(O)—$CH_3$, —$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

Each of above terms (e.g., "alkyl," "heteroalkyl," "cycloalkyl, and "heterocycloalkyl," as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R", NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Unless otherwise explicitly defined, a "substituent group," as used herein, includes a functional group selected from one or more of the following moieties, which are defined herein: (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

Compound Activities

In one embodiment, the compounds according to the current invention target topoisomerase, preferably, bacterial topoisomerase, more preferably bacterial topoisomerase in the IA family, and most preferably, bacterial topoisomerase I such as EcTopI and MtbTopI.

In a further embodiment, the compounds inhibit the activity of topoisomerase, preferably, the type IA family of topoisomerase, more preferably, bacterial topoisomerase I such as EcTopI and MtbTopI. Additionally, in preferred embodiments, the compounds exhibit selective inhibition of bacterial topoisomerase I over DNA gyrase.

In one embodiment, the compounds have activity against bacterial pathogens, including both gram-positive and -negative bacteria. In a further embodiment, the compounds have activity against mycobacteria. In another further embodiment, the compounds have activity against *E. coli*, *Staphylococcus aureus*, *Streptococcus pneumoniae*, *Helicobacter pylori*, *Mycobacterium bovis*, *Mycobacterium africanum*, *Mycobacterium microti*, *Mycobacterium canetti*, *M. smegmatis* and/or *M. tuberculosis*, preferably, *M. tuberculosis*.

In another embodiment, the compounds have activity against drug resistant bacterial pathogens, preferably, *M. tuberculosis* and/or *Staphylococcus aureus*.

In other embodiments, the compounds have activity against non-*tuberculosis* mycobacteria (NTM), e.g., *Mycobacterium avium* complex (MAC), *Mycobacterium kansasii*, and *Mycobacterium abscessus*, and thus, can be used to treat NTM infection in a subject. NTM are all the other mycobacteria that can cause pulmonary disease. NTM can also infect skin, soft tissues and lungs of cystic fibrosis patients.

In one embodiment, the compounds are used for treatment of infections in the form of biofilms formed by mycobacteria, including TB and NTM. Such biofilms are often difficult to treat with antibiotics.

In one embodiment, the compounds inhibit the growth of bacterial pathogens, preferably, through the inhibition of topoisomerase, more preferably, through the inhibition of the type IA family of topoisomerase. In a preferred embodiment, the compounds are bactericidal by inhibiting bacterial topoisomerase I, preferably, MtbTopI.

In one embodiment, the compound NSC648059 (1) has a low micromolar inhibitory, activity ($IC_{50}$=0.8-2.0 µM) against *Escherichia coli* topoisomerase I. Structurally, 1 is a fluoroquinophenzoxazine derivative with a unique planar tetracyclic ring system, belonging to a member of an extended chemical class of fluoroquinolone antibiotics. In the clinic, fluoroquinolones including norfloxacin and ciprofloxacin (FIG. 1) represent some of the most successful antibiotic classes, whose mechanisms of action are to inhibit bacterial DNA gyrase and topoisomerase IV as well as relaxation of supercoiled DNA and thus to promote breakage of double-stranded DNA [29]. Specifically, fluoroquinophenoxazines such as A-62176 and A-85226 (FIG. 1) have been reported as antibacterial [30, 31] and anticancer [32-35] agents. For example, A-62176 exhibited good activity against several cancer cell lines with $IC_{50}$ values ranging from 0.87-4.34 µM [32].

The growth inhibition $IC_{50}$ refers to the minimum compound concentration that inhibits the growth of bacteria, preferably, growth of *M. tuberculosis*, in comparison to a control in the absence of any compounds by 50%.

In one embodiment, the compounds act as the inhibitor of bacterial topoisomerase, preferably, topoisomerase I by interacting with the enzyme alone to prevent DNA binding or by interacting with the enzyme-DNA complex to inhibit enzyme function and/or DNA cleavage and/or DNA religation. In a further embodiment, the compounds also target bacterial topoisomerase I with different substitutions/mutations located in the conserved or non-conserved sequences or motif. In a preferred embodiment, the compounds bind to the enzyme-DNA complex to form a drug-enzyme-DNA ternary structure.

In certain embodiments, the compounds exhibit antibacterial activity by perturbing the interaction of bacterial topoisomerase I, in particular, EcTopI and MtbTopI with other cellular components such as RNA polymerase, which further leads to increased susceptibility to antibacterial compounds, and reduced tolerance to challenges such as high temperature, acids, and oxidative stress.

In some embodiments, the compounds may be derived from the scaffold (I) or analogs of the scaffold (I). The compounds and analogs may display different selectivity, target specificity, binding affinity, cell penetration and retention properties while inhibiting the activity of topoisomerase, preferably, bacterial topoisomerase I, as well as inhibiting the growth of bacteria, preferably, mycobacteria, more preferably, *M. tuberculosis*. The use of mycobacteria strains with different levels of topoisomerase I expression in cell based-assays could be used to complement the enzyme-based assays to identify and optimize other analogues that can target topoisomerase I. The compounds can also be identified with other assays such as multi-stress in vitro dormancy assay and/or luminescent assay.

In one embodiment, the compounds are bactericidal and/or bacteriostatic against bacterial pathogens, including both gram-positive and -negative bacteria. The compounds are effective in eliminating bacterial pathogens under all growth condition. In a further embodiment, the compounds are bactericidal against mycobacteria. In another further embodiment, the compounds are bactericidal against *E. coli*, *Staphylococcus aureus*, *Streptococcus pneumoniae*, *Helicobacter pylori*, *M. smegmatis* or *M. tuberculosis*, preferably, *M. tuberculosis*, and MRSA.

In another embodiment, the compounds are bactericidal against drug resistant bacterial pathogens, preferably, *M. tuberculosis* and *Staphylococcus aureus*.

In other embodiments, the compounds are bactericidal and/or bacteriostatic against non-*tuberculosis* mycobacteria (NTM), e.g., *Mycobacterium avium* complex (MAC), *Mycobacterium kansasii*, and *Mycobacterium abscessus*, and thus, can be used to kill NTM in a subject.

In one embodiment, the compounds are used for treatment of infections in the form of biofilms formed by mycobacteria, including TB and NTM. Such biofilms are often difficult to treat with antibiotics.

In one embodiment, the compounds are used as antibacterial drugs in general or pathogen specific therapy. The compounds according to the current invention can be used in treatment of infectious diseases, preferably, *Tuberculosis*. In some embodiments, the compounds can be used in combination with other drugs for infectious diseases to achieve synergistic effects for overcoming the resistance problem and reducing time required for treatment. Preferably, the infectious disease is *Tuberculosis*.

In one embodiment, the molecular scaffold can lead to compounds that represent a new class of bactericidal anti-mycobacteria agents with topoisomerase I being involved in the cellular mode of action.

In one embodiment, the present invention provides the compounds and salts and derivatives thereof. Derivatives of the compounds include any pharmaceutically acceptable ester, salt of an ester, alcohol, diol, ether, aldehyde, ketone, carboxylic acid or enol of a compound that can be made from the compounds by a chemical or physical process. The compounds may be in a purified form.

Pharmaceutical Composition

In one embodiment, the current invention provides a pharmaceutical composition comprising one or more of the compounds. The composition further comprises a pharmaceutically acceptable carrier. In certain embodiments, the pharmaceutical compositions can also include additional pharmaceutically active compounds know in the art. One or more additional antibiotics may also be included in the composition. These antibiotics may be, but are not limited to, beta-lactams, macrolides, tetracyclines, quinolones, aminoglycosides, sulfonamides, glycopeptides, and oxazolidines. Moreover, the composition may be in a sterile form.

The term "carrier" refers to a diluent, adjuvant, excipient, or vehicle with which the compound is administered. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration.

In a further embodiment, the compounds are in a pharmaceutically acceptable salt form or a form of free base. Examples of pharmaceutically acceptable salts include, without limitation, the nontoxic inorganic and organic acid addition salts such as the acetate, aconate, ascorbate, benzenesulfonate, benzoate, cinnamate, citrate, embonate, enantate, formate, fumarate, glutamate, glycolate, hydrochloride, hydrobromide, lactate, maleate, alonate, mandelate, methanesulfonate, naphthalene-2-sulphonate, nitrate, perchlorate, phosphate, phthalate, salicylate, sorbate, stearate, succinate, sulphate, tartrate, toluene-p-sulphonate, and the like.

In one embodiment, the composition may further contain pharmaceutically acceptable ingredients including metal salts and buffers. Metal salts of the compounds include alkali metal salts, such as the sodium salt of a compound containing a carboxyl group. The composition may also contain other acids such as oxalic acid, which may not be considered pharmaceutically acceptable, but may be useful in the preparation of salts.

In one embodiment, the compounds may be provided in un-solvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to un-solvated forms. In addition, the compounds, their salts, and derivatives may be hydrated or anhydrous.

In one embodiment, the pharmaceutical composition comprising compounds according to the invention, together with a conventional adjuvant, carrier, or diluent, may thus be placed into the form of solids including tablets, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds.

In a further embodiment, the composition is in the powder form. The pharmaceutically accepted carrier is a finely divided solid which is in a mixture with the finely divided active compounds. In another embodiment, the composition is in the tablet form. The active component is mixed with the pharmaceutically accepted carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In a further embodiment, the composition is in other solid forms including capsules, pills, cachets, and lozenges which are suitable for oral administration.

In one embodiment, the current invention provides a pharmaceutical composition for treating conditions involving bacterial infection, preferably *Tuberculosis*.

Methods for Bacterial Topoisomerase I Inhibition

In one embodiment, the current invention also provides methods comprising the administration of an effective amount of the pharmaceutical composition for treating subjects infected with bacterial pathogens, and/or in need of inhibiting the activity of topoisomerase. The subjects may refer to any animal including, but not limited to, humans, non-human primates, rodents, and the like. In a preferred embodiment, the subject is a human. In another preferred embodiment, the human is infected with mycobacteria, in particular, *M. tuberculosis*, and NTM.

In one embodiment, the current invention provides methods for treating a patient with *Tuberculosis*, comprising the administration of the pharmaceutical composition. The composition described herein has effective antibacterial activity and are selective for bacterial topoisomerase I inhibition. In a further embodiment, the composition targets and inhibits MtbTopI.

Furthermore, it would be understood by those skilled in the art that the methods described in the present invention would not only apply to treatment in a subject, but could be applied to cell cultures, organs, tissues, or individual cells in vivo or in vitro, including tumors, and immortalized cells isolated or derived from a subject.

The present invention also provides methods of inhibiting topoisomerase in bacteria, comprising the administration of an effective amount of one or more of the compounds and/or the pharmaceutical compositions as described herein to one or more bacteria. In one embodiment, the topoisomerase is the type IA topoisomerase, preferably, bacterial topoisomerase I, more preferably, EcTopI and MtbTopI.

Formulation and Administration

In one embodiment, the effective amount of said pharmaceutical composition can be administered through oral, rectal, bronchial, nasal, topical, buccal, sub-lingual, transdermal, vaginal, intramuscular, intraperitoneal, intravenous, intra-arterial, intracerebral, interaocular administration or in a form suitable for administration by inhalation or insufflation, including powders and liquid aerosol administration, or by sustained release systems such as semipermeable matrices of solid hydrophobic polymers containing the compound(s) of the invention. Administration may be also by way of other carriers or vehicles such as patches, micelles, liposomes, vesicles, implants (e.g. microimplants), synthetic polymers, microspheres, nanoparticles, and the like.

In specific embodiments, the compounds may be administered in the range of from 0.01 mg/kg body weight to 1 g/kg body weight, preferably, 1 mg·kg to 500 mg/kg body weight, more preferably, 50 mg/kg to 500 mg/kg body weight.

In one embodiment, the composition may be formulated for parenteral administration e.g., by injection, for example, bolus injection or continuous infusion. In addition, the composition may be presented in unit dose form in ampoules, pre-filled syringes, and small volume infusion or in multi-dose containers with or without an added preservative. The compositions may be in forms of suspensions, solutions, or emulsions in oily or aqueous vehicles. The composition may further contain formulation agents such as suspending, stabilizing and/or dispersing agents. In a further embodiment, the active ingredient of the composition according to the invention may be in powder form, obtained by aseptic isolation of sterile solid or by lyophilization from solution for constitution with a suitable vehicle, e.g. sterile, pyrogen-free water, before use.

In one embodiment, the composition may be formulated in aqueous solutions for oral administration. The composition may be dissolved in suitable solutions with added suitable colorants, flavours, stabilising and thickening agents, artificial and natural sweeteners, and the like. In addition, the composition may further be dissolved in solution containing viscous material, such as natural or synthetic gums, resins, methylcellulose, sodium carboxymethylcellulose, or other well-known suspending agents.

In one embodiment, the composition is applied topically or systemically or via a combination of both. The composition may be formulated in the forms of lotion, cream, gel and the like.

In one embodiment, the composition can be applied directly to the nasal cavity by conventional means, for example with a dropper, pipette or spray. The compositions may be provided in single or multi-dose form. Administration to the respiratory tract may also be achieved by means of an aerosol folmulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin.

Furthermore, the composition may be provided in the form of a dry powder, for example a powder mix of the compound in a suitable powder base such as lactose, starch, starch derivatives such as hydroxypropylmethyl cellulose and polyvinylpyrrolidone (PVP). Conveniently, the powder carrier will form a gel in the nasal cavity. The powder composition may be presented in unit dose form for example in capsules or cartridges of, e.g., gelatin, or blister packs from which the powder may be administered by means of an inhaler.

In one embodiment, the pharmaceutical composition is provided in unit dosage forms, wherein the composition in desired form is divided into unit doses containing appropriate quantities of the active component. The unit dosage form can be a packaged preparation, the package containing discrete quantities such as packaged tablets, capsules, and powders in vials or ampoules. Moreover, the unit dosage form can be a capsule, tablet, cachet, or lozenge itself, or it can be the appropriate number of any of these in packaged form. In a preferred embodiment, tablet or capsule forms are for oral administration and liquid form are for intravenous administration and continuous infusion.

The present invention also provides kits comprising the compounds and/or pharmaceutical compositions as described herein. The kits may further be used in the methods described herein. The kits may also include at least one reagent and/or instruction for their use. Moreover, the kits may include one or more containers filled with one or more compounds and/or pharmaceutical composition described in the present invention. The kits may also comprise a control composition, such as a control antibiotic.

The following are examples that illustrate the aforementioned embodiments and should not be construed as limiting.

EXAMPLES

It should be understood that the examples and embodiments described herein are for illustrative purposes only and that various modifications or changes in light thereof will be suggested to persons skilled in the art and are to be included within the spirit and purview of this application.

Example 1—General Methods for Chemistry

All reagents and anhydrous solvents were purchased from Sigma-Aldrich and Fisher Scientific, and were used without further purification. All reactions were monitored either by thin-layer chromatography (TLC) or by analytical high performance liquid chromatography (HPLC) to detect the completion of reactions. TLC was performed using glass plates pre-coated with silica gel (0.25 mm, 60-Å pore size, 230-400 mesh, Sorbent Technologies, GA) impregnated with a fluorescent indicator (254 nm). TLC plates were visualized by exposure to ultraviolet light (UV). Hydrogenation reactions were performed employing domnick hunter NITROX UHP-60H hydrogen generator, USA. Microwave synthesis was performed using Biotage Initiator 8 Exp Microwave System. Compounds were purified by flash column chromatography on silica gel using a Biotage Isolera One system and a Biotage SNAP cartridge. $^1$H and $^{13}$C NMR spectra were obtained on a Bruker Avance DRX-400 instrument with chemical shifts (δ, ppm) determined using TMS as internal standard. Coupling constants (J) are in hertz (Hz). ESI mass spectra in either positive or negative mode were provided by Varian 500-MS IT Mass Spectrometer. High-resolution mass spectra (HRMS) were obtained on an Agilent 6530 Accurate Mass Q-TOF LC/MS. The purity of compounds was determined by analytical HPLC using a Gemini, 3 μm, C18, 110 Å column (50 mm×4.6 mm, Phenomenex) and a flow rate of 1.0 mL/min. Gradient conditions: solvent A (0.1% trifluoroacetic acid in water) and solvent B (acetonitrile): 0-2.00 min 100% A, 2.00-7.00 min 0-100% B (linear gradient), 7.00-8.00 min 100% B, UV detection at 254 and 220 nm.

6-Amino-2,3-difluorophenol (2)

2,3-Difluoro-6-nitrophenol (700 mg, 4 mmol) was dissolved in ethanol (5 mL) and palladium on activated carbon (Pd/C) (84.8 mg, 20%) was added. The reaction was stirred at room temperature under $H_2$ atmosphere (1.0 bar). After 7 h, all starting material was consumed and Pd/C was filtered through Celite. The solvent was evaporated under reduced pressure to afford 6-amino-2,3-difluorophenol (550.5 mg, 95% yield). $^1$H NMR (400 MHz, $CDCl_3$): δ (ppm) 6.59 (dt, J=9.9, 8.6 Hz, 1H), 6.47-6.31 (m, 1H), 4.27 (br s, 2H). ESI-HRMS: calc. for $C_6H_6F_2NO$ [M+H]$^+$: 146.0412, found: 146.0418.

Diethyl 2-(((3, 4-d fluoro-2-hydroxyphenyl)amino) methylene)malonate (3)

6-Amino-2,3-difluorophenol (2) (550 mg, 3.8 mmol) was dissolved in ethanol (15 mL) and diethyl 2-(ethoxymethylene)malonate (819 mg, 3.8 mmol) was added. The reaction was stirred at room temperature until there was no starting material left. Ethanol was removed and the residue was purified by flash column chromatography on silica gel (EtOAc/hexane=1/3 to 3/1) to give product 3 as a brown solid (1.04 g, 87%). $^1$H NMR (400 MHz, d$_6$-DMSO): δ (ppm) 10.96 (d, J=14.0 Hz, 1H), 8.45 (d, J=13.9 Hz, 1H), 7.31-7.22 (m, 1H), 6.98-6.86 (m, 1H), 4.20 (q, J=7.1 Hz, 2H), 4.12 (q, J=7.1 Hz, 2H), 1.26 (t, J=7.1 Hz, 3H), 1.24 (t, J=7.1 Hz, 3H). ESI-MS: calc. for C$_{14}$H$_{14}$F$_2$NO$_5$ [M−H]$^−$: 314.3, found: 314.3.

Ethyl 6, 7-difluoro-8-hydroxy-4-oxo-1, 4-dihydro-quinoline-3-carboxylate (4)

Compound 3 (445 mg, 1.4 mmol) was added in a microwave sealed tube. Diphenyl ether (2.5 mL) was added and the tube was sealed with cap. The reaction was then set up at 250° C. in a Biotage Microwave Initiator instrument for 30 min. Hexane was added and the solid was filtered and washed with hexane. The product was then dried and obtained in 80% yield (299.4 mg), which was used for next step without further purification. $^1$H NMR (400 MHz, d$_6$-DMSO): δ (ppm) 8.36 (s, 1H), 7.45 (dd, J=10.9, 7.9 Hz, 1H), 4.21 (q, J=7.1 Hz, 2H), 1.27 (t, J=7.1 Hz, 3H). ESI-MS: calc. for C$_{12}$HF$_2$NO$_4$ [M−H]$^−$: 268.2, found: 268.2.

Ethyl 5,6-difluoro-9-nitro-3-oxo-3H-pyrido[3,2,1-kl]phenoxazine-2-carboxylate (6a)

Compound 4 (269 mg, 1 mmol) and 1-chloro-2,4-dinitrobenzene (202 mg, 1 mmol) were dissolved in DMF (2 mL). NaHCO$_3$ (252 mg, 3 mmol) was added and the reaction was stirred at 100° C. until no starting materials were detected by HPLC. The solid base was removed by filtration through Celite. The filtrate was concentrated and the residue was purified through Biotage reverse phase C18 cartridge to give 220 mg of 6a as yellow solid (yield: 57%). $^1$H NMR (400 MHz, d$_6$-DMSO): δ (ppm) 9.01 (s, 1H), 8.15 (d, J=9.6 Hz, 1H), 8.05-8.01 (m, 2H), 7.60-7.54 (m, 1H), 4.27 (q, J=7.2 Hz, 2H), 1.32 (t, J=7.2 Hz, 3H); $^{13}$C NMR (100 MHz, d$_6$-DMSO): δ (ppm) 170.4, 163.7, 145.8, 142.7, 138.1, 133.2, 129.4, 124.6, 122.2, 120.8, 117.0, 113.0, 105.4, 105.2, 60.8, 14.2; ESI-MS: calc. for C$_{18}$H$_{10}$F$_2$N$_2$O$_6$Na [M+Na]$^+$: 411.3, found: 411.2. ESI-HRMS: calc. for C$_{18}$H$_{11}$F$_2$N$_2$O$_6$[M+H]$^+$: 389.0580, found: 389.0582. HPLC purity: 100% (254 nm), t$_R$: 6.92 min; 100% (220 nm), t$_R$: 6.92 min.

Compounds 6b-e were prepared according to the experimental procedure above for the preparation of 6a.

Ethyl 9-cyano-5, 6-difluoro-3-oxo-3H-pyrido[3, 2, 1-kl]phenoxazine-2-carboxylate (6b)

Yellow solid. Yield: 59%. $^1$H NMR (400 MHz, d$_6$-DMSO): δ (ppm) 9.04 (s, 1H), 8.11 (d, J=8.8 Hz, 1H), 7.87 (d, J=1.6 Hz, 1H), 7.72 (dd, J=1.6 and 8.8 Hz, 1H), 7.63-7.59 (m, 1H), 4.28 (q, J=7.2 Hz, 2H), 1.31 (t, J=7.2 Hz, 3H); ESI-MS: calc. for C$_{19}$H$_{10}$F$_2$N$_2$O$_4$Na [M+Na]$^+$: 391.3, found: 391.2. ESI-HRMS: calc. for C$_{19}$H$_{11}$F$_2$N$_2$O$_4$ [M+H]$^+$: 369.0681, found: 369.0684. HPLC purity: 100% (254 nm), t$_R$: 6.73 min; 100% (220 nm), t$_R$: 6.73 min.

Ethyl 5, 6-difluoro-3-oxo-9-(trifluoromethyl)-3H-pyrido[3, 2, l-kl]phenoxazine-2-carboxylate (6c)

Yellow solid. Yield: 10%. $^1$H NMR (400 MHz, d$_6$-DMSO): δ (ppm) 9.05 (s, 1H), 8.12 (d, J=8.8 Hz, 1H), 7.71 (d, J=1.6 Hz, 1H), 7.63-7.58 (m, 2H), 4.27 (q, J=7.2 Hz, 2H), 1.32 (t, J=7.2 Hz, 3H). ESI-MS: calc. for C$_{19}$H$_{10}$F$_5$NO$_4$Na [M+Na]$^+$: 434.3, found: 434.1. ESI-HRMS: calc. for C$_{19}$H$_{11}$F$_5$NO$_4$ [M+H]$^+$: 412.0603, found: 412.0603. HPLC purity: 100% (254 nm), t$_R$: 7.25 min; 100% (220 nm), t$_R$: 7.25 min.

Ethyl 9-acetyl-5, 6-difluoro-3-oxo-3H-pyrido[3, 2, 1-kl]phenoxazine-2-carboxylate (6d)

Dark yellow solid. Yield: 38%. $^1$H NMR (400 MHz, d$_6$-DMSO): δ (ppm) 8.97 (s, 1H), 8.06-7.93 (m, 1H), 7.73 (d, J=8.4 Hz, 1H), 7.69 (s, 1H), 7.55 (dd, J=10.2, 8.0 Hz, 1H), 4.27 (q, J=7.1 Hz, 2H), 2.58 (s, 3H), 1.33 (t, J=7.1 Hz, 3H). ESI-MS: calc. for C$_{20}$H$_{13}$F$_2$NNaO$_5$ [M+Na]$^+$: 408.3, found: 408.1. HPLC purity: 100% (254 nm), t$_R$: 6.62 min; 100% (220 nm), t$_R$: 6.62 min.

Ethyl 10-chloro-5, 6-difluoro-9-nitro-3-oxo-3H-pyrido[3, 2, 1-kl]phenoxazine-2-carboxylate (6e)

Dark yellow solid. Yield: 40%. $^1$H NMR (400 MHz, d$_6$-DMSO): δ (ppm) 9.13 (s, 1H), 8.48 (s, 1H), 8.12 (s, 1H), 7.69-7.60 (m, 1H), 4.30 (q, J=7.0 Hz, 2H), 1.33 (t, J=7.1 Hz, 3H). ESI-MS: calc. for C$_{18}$H$_9$ClF$_2$N$_2$NaO$_6$ [M+Na]$^+$: 445.0, found: 445.1. HPLC purity: 98.5% (254 nm), t$_R$: 6.92 min; 96.9% (220 nm), t$_R$: 6.92 min.

5, 6-Difluoro-9-nitro-3-oxo-3H-pyrido[3, 2,1-kl]phenoxazine-2-carboxylic acid (7a)

Compound 6a (180 mg, 0.46 mmol) was dissolved in AcOH (15 mL). Hydrochloric acid (1 N, 2 mL) was added and the reaction was stirred under reflux for 2 h. Upon completion, water was added and yellow solid was precipitated. The solid was collected by filtration and washed with water, then dried and afforded product 7a (150 mg) as yellow solid in 91% yield. $^1$H NMR (400 MHz, d$_6$-DMSO): δ (ppm) 9.36 (s, 1H), 8.42 (d, J=9.2 Hz, 1H), 8.17 (d, J=2.8 Hz, 1H), 8.09 (dd, J=2.4 and 9.2 Hz, 1H), 7.86-7.82 (m, 1H); ESI-MS: calc. for C$_{16}$H$_7$F$_2$N$_2$O$_6$ [M+H]$^+$: 361.2, found: 361.3. ESI-HRMS: calc. for C$_{16}$H$_{17}$F$_2$N$_2$O$_6$[M+H]$^+$: 361.0267, found: 361.0268. HPLC purity: 100% (254 nm), t$_R$: 6.79 min; 100% (220 nm), t$_R$: 6.79 min.

Compounds 7b-e were prepared according to the experimental procedure above for the preparation of 7a.

9-Cyano-5, 6-d fluoro-3-oxo-3H-pyrido[3, 2, 1-d]phenoxazine-2-carboxylic acid (7b)

Yellow solid. Yield: 36%. $^1$H NMR (400 MHz, d$_6$-DMSO): δ (ppm) 9.34 (s, 1H), 8.35 (d, J=8.8 Hz, 1H), 7.98 (d, J=1.6 Hz, 1H), 7.82 (d, J=2.4 Hz, 1H), 7.78-7.75 (m, 2H); ESI-MS: calc. for C$_{17}$H$_7$F$_2$N$_2$O$_4$[M+H]$^+$: 341.2, found: 341.1. ESI-HRMS: calc. for C$_{17}$H$_7$F$_2$N$_2$O$_4$ [M+H]$^+$: 341.0368, found: 341.0378. HPLC purity: 95.1% (254 nm), t$_R$: 6.37 min; 97.7% (220 nm), t$_R$: 6.37 min.

5, 6-Difluoro-3-oxo-9-(trifluoromethyl)-3H-pyrido[3, 2,1-kl]phenoxazine-2-carboxylic acid (7c)

Yellow solid. Yield: 95%. $^1$H NMR (400 MHz, d$_6$-DMSO): δ (ppm) 9.35 (s, 1H), 8.37 (d, J=8.4 Hz, 1H), 7.84-7.79 (m, 2H), 7.65-7.62 (dd, J=1.2 and 8.8 Hz, 1H); ESI-MS: calc. for C$_{17}$H$_7$F$_5$NO$_4$ [M+H]$^+$: 384.2, found: 384.1. ESI-HRMS: calc. for C$_{17}$H$_7$F$_5$NO$_4$ [M+H]$^+$: 384.0290, found: 384.0293. HPLC purity: 100% (254 nm), t$_R$: 7.15 min; 100% (220 nm), t$_R$: 7.15 min.

9-Acetyl-5, 6-difluoro-3-oxo-3H-pyrido[3,2, 1-kl]phenoxazine-2-carboxylic acid (7d)

Yellow solid. Yield: 62%. $^1$H NMR (400 MHz, d$_6$-DMSO): δ (ppm) 9.36 (s, 1H), 8.30 (d, J=11.2 Hz, 1H), 7.85-7.80 (m, 3H), 2.63 (s, 3H); ESI-MS: calc. for C$_{18}$H$_{10}$F$_2$NO$_5$ [M+H]$^+$: 358.3, found: 358.2. ESI-HRMS: calc. for C$_{18}$H$_{10}$F$_2$NO$_5$ [M+H]$^+$: 358.0522, found: 358.0521. HPLC purity: 97.3% (254 nm), t$_R$: 6.70 min; 97.2% (220 nm), t$_R$: 6.70 min.

10-Chloro-5, 6-difluoro-9-nitro-3-oxo-3H-pyrido[3, 2, 1-kl]phenoxazine-2-carboxylic acid (7e)

Brown solid. Yield: 39%. $^1$H NMR (400 MHz, d$_6$-DMSO): δ (ppm) 9.43 (s, 1H), 8.74 (s, 1H), 8.18 (s, 1H), 7.83-7.79 (m, 1H); ESI-MS: calc. for C$_{16}$H$_6$ClF$_2$N$_2$O$_6$ [M+H]$^+$: 394.7, found: 394.9. ESI-HRMS: calc. for C$_6$H$_6$F$_2$N$_2$O$_6$ [M+H]$^+$: 394.9877, found: 394.9879. HPLC purity: 95.4% (254 nm), t$_R$: 6.90 min; 97.0% (220 nm), t$_R$: 6.90 min.

9-Amino-5, 6-difluoro-3-oxo-3H-pyrido[3, 2,1-kl]phenoxazine-2-carboxylic acid (1)

Compound 7a (150 mg, 0.42 mmol) was added to a mixture of AcOH/HCl (1/1). SnCl$_2$ (236 mg, 1.25 mmol) was added and the reaction was stirred under reflux for 2 h. No starting material was observed in the reaction and then water was added. The large amount of solid precipitated and was collected by filtration. Product 1 was obtained in 86% yield (236 mg) as yellow solid. $^1$H NMR (400 MHz, d$_6$-DMSO): δ (ppm) 9.08 (s, 1H), 7.79 (d, J=9.2 Hz, 1H), 7.76-7.73 (m, 1H), 6.48 (dd, J=2.4 and 9.2 Hz, 1H), 6.43 (d, J=2.4 Hz, 1H); ESI-MS: calc. for C$_{16}$H$_9$F$_2$N$_2$O$_4$ [M+H]$^+$: 331.3, found: 331.1. ESI-HRMS: calc. for C$_{16}$H$_9$F$_2$N$_2$O$_4$ [M+H]$^+$: 331.0525, found: 331.0526. HPLC purity: 100% (254 nm), t$_R$: 6.47 min; 100% (220 nm), t$_R$: 6.47 min.

Ethyl-5-fluoro-6-(4-methylpiperazin-1-yl)-9-nitro-3-oxo-3H-pyrido[3, 2, 1-kl]phenoxazine-2-carboxylate (9)

Compound 6a (159 mg, 0.4 mmol) was dissolved in pyridine (1 mL) and 1-methylpiperazine (120 mg, 1.2 mmol) was added. The reaction was heated to 110° C. until no starting material was observed. Pyridine was removed under reduced pressure and the residue was purified by flash column chromatography on silica gel (MeOH/CH$_2$Cl$_2$=1/19), affording product 9 (100.1 mg) in 53% yield as orange solid. $^1$H NMR (400 MHz, d$_6$-DMSO): δ (ppm) 8.87 (d, J=1.6 Hz, 1H), 8.04-7.97 (m, 2H), 7.87 (t, J=1.2 Hz, 1H), 7.32 (dd, J=1.2 and 8.0 Hz, 2H), 4.25 (q, J=7.2 Hz, 2H), 3.34 (s, 4H), 3.27 (s, 4H), 2.27 (s, 3H), 1.32 (t, J=7.2 Hz, 3H); ESI-MS: calc. for C$_{23}$H$_{22}$FN$_4$O$_6$[M+H]$^+$: 469.4, found: 469.3. HPLC purity: 100% (254 nm), t$_R$: 5.48 min; 100% (220 nm), t$_R$: 5.48 min.

5-Fluoro-6-(4-methylpiperazin-1-yl)-9-nitro-3-oxo-3H-pyrido[3, 2,1-kl]phenoxazine-2-carboxylic acid (10a)

Compound 7a (108 mg, 0.3 mmol) was dissolved in pyridine (4 mL), and then the reaction was heated to 90° C. 1-Methylpiperazine (100 μL, 0.9 mmol) was added and the reaction was stirred under nitrogen atmosphere until there was no starting material. Upon completion, pyridine was removed under reduced pressure and the residue was dissolved in ethanol (10 mL) and heated under reflux for additional 30 min. The solid was filtered and washed with water, then dried to obtain product 10a (60 mg) in 45% yield as yellow solid. $^1$H NMR (400 MHz, d$_6$-DMSO): δ (ppm) 9.18 (s, 1H), 8.29 (d, J=8.0 Hz, 1H), 8.02-7.99 (m, 2H), 7.53 (d, J=12.6 Hz, 1H), 3.30 (br s, overlapping with H$_2$O peak, 4H), 2.57 (br s, 4H), 2.32 (s, 3H); ESI-MS: calc. for C$_{21}$H$_{18}$FN$_4$O$_6$[M+H]$^+$: 441.4, found: 441.4. ESI-MS: calc. for C$_{21}$H$_{18}$FN$_4$O$_6$[M+H]$^+$: 441.1205, found: 441.1216. HPLC purity: 100% (254 nm), t$_R$: 5.37 min; 100% (220 nm), t$_R$: 5.37 min.

Compounds 10b and 11a-k were prepared following the similar procedure for the preparation of 10a.

5-Fluoro-9-nitro-3-oxo-6-(piperazin-1-yl)-3H-pyrido[3, 2, 1-kl]phenoxazine-2-carboxylic acid (10b)

Yellow solid. Yield: 84%. $^1$H NMR (400 MHz, d$_6$-DMSO): δ (ppm) 8.94 (s, 1H), 7.66 (d, J=8.8 Hz, 1H), 7.45 (d, J=12.0 Hz, 1H), 6.43-6.36 (m, 2H), 3.22 (s, 4H), 2.87 (s, 4H); ESI-MS: calc. for C$_{20}$H$_{16}$FN$_4$O$_6$[M+H]$^+$: 427.4, found: 427.2. ESI-HRMS: calc. for C$_{20}$H$_{16}$FN$_4$O$_6$ [M+H]$^+$: 427.1048, found: 427.1041. HPLC purity: 100% (254 nm), t$_R$: 5.36 min; 100% (220 nm), t$_R$: 5.36 min.

9-Amino-5-fluoro-6-(4-methylpiperazin-1-yl)-3-oxo-3H-pyrido[3,2,1-kl]phenoxazine-2-carboxylic acid (11a)

Yellow solid. Yield: 48%. $^1$H NMR (400 MHz, d$_6$-DMSO): δ (ppm) 8.94 (s, 1H), 7.65 (d, J=9.2 Hz, 1H), 7.45 (d, J=12.0 Hz, 1H), 6.43-6.36 (m, 2H), 5.77 (s, 2H), 3.31 (s, 4H), 2.57 (s, 4H), 2.32 (s, 3H); ESI-MS: calc. for C$_{21}$H$_{20}$FN$_4$O$_4$[M+H]$^+$: 411.4, found: 411.2. ESI-MS: calc. for C$_{21}$H$_{20}$FN$_4$O$_4$[M+H]$^+$: 411.1463, found: 411.1466. HPLC purity: 100% (254 nm), t$_R$: 5.22 min; 100% (220 nm), t$_R$: 5.22 min.

9-Amino-5-fluoro-3-oxo-6-(piperazin-1-yl)-3H-pyrido[3,2, 1-kl]phenoxazine-2-carboxylic acid (11b)

Yellow solid. Yield: 97%. $^1$H NMR (400 MHz, d$_6$-DMSO): δ (ppm) 8.97 (s, 1H), 7.68 (d, J=9.2 Hz, 1H), 7.48 (d, J=12.4 Hz, 1H), 6.44-6.38 (m, 2H), 5.77 (s, 2H), 3.22 (s, 4H), 2.86 (s, 4H); ESI-MS: calc. for C$_{20}$H$_{18}$FN$_4$O$_4$ [M+H]$^+$: 397.4, found: 397.2. ESI-HRMS: calc. for C$_{20}$H$_{18}$FN$_4$O$_4$[M+H]$^+$: 397.1307, found: 397.1303. HPLC purity: 100% (254 nm), 100% (220 nm), t$_R$: 5.20 min.

9-Amino-5-fluoro-6-(4-methylpiperidin-1-yl)-3-oxo-3H-pyrido[3, 2, 1-kl]phenoxazine-2-carboxylic acid (11c)

Yellow solid. Yield: 33%. $^1$H NMR (400 MHz, d$_6$-DMSO): δ (ppm) 8.92 (s, 1H), 7.63 (d, J=8.0 Hz, 1H), 7.43 (d, J=11.6 Hz, 1H), 6.42-6.36 (m, 2H), 5.75 (s, 2H), 3.13 (t, J=10.8 Hz, 2H), 1.71 (d, J=11.2 Hz, 2H), 1.57 (s, 1H), 1.32-1.26 (m, 2H), 0.98 (s, 3H); $^{13}$C NMR (100 MHz, d$_6$-DMSO): δ (ppm) 175.4, 166.4, 150.7, 144.6, 138.5, 136.0, 131.7, 125.3, 119.6, 119.5, 117.6, 112.2, 111.1, 107.0, 104.0, 101.2, 51.1, 35.1, 30.6, 22.5; ESI-MS: calc. for C$_{22}$H$_{21}$FN$_3$O$_4$ [M+H]$^+$: 410.4, found: 410.2. ESI-HRMS:

calc. for C$_{22}$H$_{21}$FN$_3$O$_4$[M+H]$^+$: 410.1511, found: 410.1510. HPLC purity: 100% (254 nm), t$_R$: 6.38 min; 100% (220 nm), t$_R$: 6.38 min.

9-Amino-5-fluoro-6-morpholino-3-oxo-3H-pyrido[3,2,1-kl]phenoxazine-2-carboxylic acid (11d)

Yellow solid. Yield: 71%. $^1$H NMR (400 MHz, d$_6$-DMSO): δ (ppm) 8.93 (s, 1H), 7.64 (d, J=8.8 Hz, 1H), 7.45 (d, J=12.0 Hz, 1H), 6.43-6.37 (m, 2H), 5.75 (s, 2H), 3.69 (s, 4H), 3.28 (s, 4H); ESI-MS: calc. for C$_{20}$H$_{17}$FN$_3$O$_5$ [M+H]$^+$: 398.4, found: 398.2. ESI-HRMS: calc. for C$_{20}$H$_{17}$FN$_3$O$_5$[M+H]$^+$: 398.1147, found: 398.1146. HPLC purity: 100% (254 nm), t$_R$: 6.38 min; 100% (220 nm), t$_R$: 6.38 min.

9-Amino-S-fluoro-3-oxo-6-(phenethylamino)-3H-pyrido[3,2,1-kl]phenoxazine-2-carboxylic acid (11e)

Yellow solid. Yield: 55%. $^1$H NMR (400 MHz, d$_6$-DMSO): δ (ppm) 8.90 (s, 1H), 7.61 (d, J=9.2 Hz, 1H), 7.45 (d, J=13.2 Hz, 1H), 7.29-7.18 (m, 5H), 6.43-6.37 (m, 2H), 6.15 (br s, 1H), 5.76 (br s, 2H), 3.68-3.61 (m, 2H), 2.89-2.85 (m, 2H); ESI-MS: calc. for C$_{24}$H$_{18}$FN$_3$O$_4$[M+H]$^+$: 432.4, found: 432.1. ESI-HRMS: calc. for C$_{24}$H$_{19}$FN$_3$O$_4$[M+H]$^+$: 432.1354, found: 432.1362. HPLC purity: 100% (254 nm), t$_R$: 7.07 min; 100% (220 nm), t$_R$: 7.07 min.

6-(((3s,5s,7s)-Adamantan-1-yl)amino)-9-amino-5-fluoro-3-oxo-3H-pyrido[3,2,1-kl]phenoxazine-2-carboxylic acid (11f)

Brown solid. Yield: 29%. $^1$H NMR (400 MHz, d$_6$-DMSO): δ (ppm) 9.00 (s, 1H), 7.71 (d, J=9.1 Hz, 1H), 7.54 (d, J=10.7 Hz, 1H), 6.50-6.38 (m, 2H), 5.81 (s, 2H), 4.34 (s, 1H), 2.09-2.04 (m, 3H), 1.85 (s, 6H), 1.65-1.55 (m, 6H). ESI-MS: calc. for C$_{26}$H$_{23}$FN$_3$O$_4$[M−H]$^+$: 460.2, found: 460.0. HPLC purity: 85.2% (254 nm), t$_R$: 7.41 min; 91.1% (220 nm), t$_R$: 7.41 min.

6-([1,4'-Bipiperidin]-1'-yl)-9-amino-5-fluoro-3-oxo-3H-pyrido[3,2,1-kl]phenoxazine-2-carboxylic acid (11g)

Yellow solid. Yield: 64%. $^1$H NMR (400 MHz, d$_6$-DMSO): δ (ppm) 8.98 (s, 1H), 7.68 (d, J=4.0 Hz, 1H), 7.49 (d, J=9.6 Hz, 1H), 6.45-6.41 (m, 2H), 5.77 (br s, 2H), 3.20-3.15 (m, 1H), 1.84-1.82 (m, 3H), 1.64-1.41 (m, 14H), 1.06-1.04 (m, 1H); ESI-MS: calc. for C$_{26}$H$_{28}$FN$_4$O$_4$[M+H]$^+$: 479.5, found: 479.3. ESI-HRMS: calc. for C$_{26}$H$_{28}$FN$_4$O$_4$[M+H]$^+$: 479.2089, found: 479.2093. HPLC purity: 100% (254 nm), t$_R$: 5.53 min; 100% (220 nm), t$_R$: 5.53 min.

9-Amino-5-fluoro-6-((2-morpholinoethyl)amino)-3-oxo-3H-pyrido[3,2,1-kl]phenoxazine-2-carboxylic acid (11h)

Yellow solid. Yield: 74%. $^1$H NMR (400 MHz, d$_6$-DMSO): δ (ppm) 8.90 (s, 1H), 8.55 (s, 1H), 7.46 (d, J=6.0 Hz, 1H), 7.39-7.34 (m, 2H), 6.42-6.37 (m, 2H), 5.95 (s, 1H), 5.78 (br s, 2H), 2.57 (s, 2H), 2.44 (br s, 6H); ESI-MS: calc. for C$_{22}$H$_{22}$FN$_4$O$_5$[M+H]$^+$: 441.4, found: 441.3. ESI-calc. for C$_{22}$H$_{22}$FN$_4$O$_5$[M+H]$^+$: 441.1569, found: 441.1579. HPLC purity: 97.2% (254 nm), t$_R$: 5.22 min; 99.3% (220 nm), t$_R$: 5.22 min.

9-Amino-6-(cyclohexylamino)-5-fluoro-3-oxo-3H-pyrido[3,2,1-kl]phenoxazine-2-carboxylic acid (11i)

Brown solid. Yield: 74%. $^1$H NMR (400 MHz, d$_6$-DMSO): δ (ppm) 8.86 (s, 1H), 7.58-7.56 (m, 1H), 7.43-7.40 (m, 1H), 6.40 (s, 1H), 5.72 (s, 2H), 5.40-5.38 (m, 1H), 1.92 (s, 3H), 1.73-1.67 (m, 3H), 1.31-1.22 (m, 6H); ESI-MS: calc. for C$_{22}$H$_{21}$FN$_3$O$_4$ [M+H]$^+$: 410.4, found: 410.3. ESI-HRMS: calc. for C2H$_{21}$FN$_3$O$_4$[M+H]$^+$: 410.1511, found: 410.1494. HPLC purity: 100% (254 nm), t$_R$: 7.27 min; 100% (220 nm), t$_R$: 7.27 min.

9-Amino-6-(cyclopentylamino)-5-fluoro-3-oxo-3H-pyrido[3,2,1-kl]phenoxazine-2-carboxylic acid (11j)

Black solid. Yield: 63%. $^1$H NMR (400 MHz, d$_6$-DMSO): δ (ppm) 8.91 (s, 1H), 7.62 (d, J=8.8 Hz, 1H), 7.47 (d, J=12.4 Hz, 1H), 6.46-6.41 (m, 2H), 5.73 (s, 2H), 5.53 (d, J=2.4 Hz, 1H), 4.30 (s, 1H), 1.93 (br s, 4H), 1.73 (br s, 4H); ESI-MS: calc. for C$_{21}$H$_{19}$FN$_3$O$_4$[M+H]$^+$: 396.4, found: 396.1. ESI-HRMS: calc. for C$_{21}$H$_{19}$FN$_3$O$_4$[M+H]$^+$: 396.1354, found: 396.1358. HPLC purity: 96.7% (254 nm), t$_R$: 7.07 min; 96.0% (220 nm), t$_R$: 7.06 min.

9-Amino-5-fluoro-6-(hexylamino)-3-oxo-3H-pyrido[3,2,1-kl]phenoxazine-2-carboxylic acid (11k)

Yellow solid. Yield: 49%. $^1$H NMR (400 MHz, d$_6$-DMSO): δ (ppm) 8.88 (s, 1H), 7.64 (s, 1H), 7.44 (s, 1H), 6.56-6.36 (m, 2H), 5.88-5.50 (m, 2H), 1.57 (s, 2H), 1.27 (s, 7H), 0.84 (s, 4H); ESI-MS: calc. for C$_{22}$H$_{23}$FN$_3$O$_4$[M+H]$^+$: 412.4, found: 412.2. ESI-HRMS: calc. for C$_{22}$H$_{23}$FN$_3$O$_4$ [M+H]$^+$: 412.1667, found: 412.1672. HPLC purity: 100% (254 nm), t$_R$: 7.47 min; 100% (220 nm), t$_R$: 7.47 min.

9-acetamido-5,6-difluoro-3-oxo-3H-pyrido[3,2,1-kl]phenoxazine-2-carboxylic acid (12)

To the solution of 1 (33 mg, 0.1 mmol) and pyridine (1 mL), acetic anhydride (12.2 mg, 0.12 mmol) was added. The reaction was stirred at 80° C. for 3 h, then at 100° C. until no starting material was detected by HPLC. The solid was filtered and dried to give 34.1 mg of 12 in 92% yield. Yellow solid. $^1$H NMR (400 MHz, d$_6$-DMSO): δ (ppm) 10.31 (s, 1H), 9.20 (s, 1H), 8.05 (d, J=9.2 Hz, 1H), 7.78 (t, J=8.0 Hz, 1H), 7.66 (s, 1H), 7.29 (d, J=7.6 Hz, 1H), 2.06 (s, 3H); ESI-MS: calc. for C$_{18}$H$_{11}$F$_2$N$_2$O$_5$[M+H]$^+$: 373.3, found: 373.2. ESI-MS: calc. for C$_{18}$H$_{11}$F$_2$N$_2$O$_5$ [M+H]$^+$: 373.0631, found: 373.0638. HPLC purity: 98.6% (254 nm), t$_R$: 6.42 min; 99.1% (220 nm), t$_R$: 6.42 min.

Compounds 14 and 15a-b were prepared at 70° C. following the similar procedure for the preparation of 10a

(S)-9-amino-6-(3-((tert-butoxycarbonyl)amino)pyrrolidin-1-yl)-S-fluoro-3-oxo-3H-pyrido[3,2,1-kl]phenoxazine-2-carboxylic acid (15a)

Yellow solid. Yield: 86%. $^1$H NMR (400 MHz, d$_6$-DMSO): δ (ppm) 8.77 (s, 1H), 7.49 (d, J=9.6 Hz, 1H), 7.31 (d, J=14.0 Hz, 1H), 7.17 (d, J=5.6 Hz, 1H), 6.38 (dd, J=2.4 and 9.2 Hz, 2H), 6.29 (d, J=2.0 Hz, 1H), 5.67 (s, 2H), 3.82-3.80 (m, 5H), 2.05-2.04 (m, 1H), 1.83 (br s, 1H), 1.38 (s, 9H); ESI-MS: calc. for C$_{25}$H$_{26}$FN$_4$O$_6$[M+H]$^+$: 497.5, found: 497.3. ESI-HRMS: calc. for C$_{25}$H$_{26}$FN$_4$O$_6$[M+H]$^+$:

(S)-6-(3-aminopyrrolidin-1-yl)-5-fluoro-9-nitro-3-oxo-3H-pyrido[3,2,1-kl]phenoxazine-2-carboxylic acid (16)

Compound 16 was prepared following the same procedure for the synthesis of 7. Brown solid. Yield: 32% (two steps). $^1$H NMR (400 MHz, $d_6$-DMSO): δ (ppm) 9.10 (s, 1H), 8.41 (s, 2H), 8.25 (d, J=9.3 Hz, 1H), 8.09 (s, 1H), 8.01 (d, J=7.2 Hz, 1H), 7.48 (d, J=13.6 Hz, 1H), 4.07-3.74 (m, 5H), 2.28 (s, 1H), 2.08 (s, 1H). ESI-MS: calc. for $C_{20}H_{16}FN_4O_6[M+H]^+$: 427.4, found: 427.1. HPLC purity: 100% (254 nm), $t_R$: 5.45 min; 100% (220 nm), $t_R$: 5.46 min.

(S)-9-amino-6-(3-aminopyrrolidin-1-yl)-S-fluoro-3-oxo-3H-pyrido[3, 2,1-kl]phenoxazine-2-carboxylic acid (17a)

Compound 15a (85 mg, 0.17 mmol) was dissolved in 10 mL of hydrochloric acid (1 N). The reaction was stirred under reflux for 2.5 h. The solvent was removed and ethanol (10 mL) was added. The mixture was heated under reflux for 30 min. The solid was collected by filtration and dried to yield 52 mg of 17a in 78% yield. Yellow solid. $^1$H NMR (400 MHz, $d_6$-DMSO): δ (ppm) 8.94 (s, 1H), 8.24 (s, 3H), 7.65 (d, J=9.2 Hz, 1H), 7.50 (d, J=13.6 Hz, 1H), 6.46-6.40 (m, 2H), 3.99-3.85 (m, 5H), 2.34-2.26 (m, 1H), 2.09-1.98 (m, 1H); ESI-MS: calc. for $C_{20}H_{18}FN_4O_4[M+H]^+$: 397.4, found: 397.1. ESI-MS: calc. for $C_{20}H_{18}FN_4O_4[M+H]^+$: 397.1307, found: 397.1298. HPLC purity: 100% (254 nm), $t_R$: 5.20 min; 100% (220 nm), $t_R$: 5.20 min.

(R)-9-amino-6-(3-aminopyrrolidin-1-yl)-5-fluoro-3-oxo-3H-pyrido[3, 2, 1-kl]phenoxazine-2-carboxylic acid (17b)

Compound 17b was prepared using the same procedure for the synthesis of 17a. Brown solid. Yield: 48% (two steps). $^1$H NMR (400 MHz, $d_6$-DMSO): δ (ppm) 8.88 (s, 1H), 8.31 (s, 3H), 7.59 (d, J=9.2 Hz, 1H), 7.43 (d, J=13.2 Hz, 1H), 6.42 (d, J=9.2 Hz, 1H), 6.38 (s, 1H), 3.98-3.88 (m, 2H), 3.73-3.68 (m, 3H), 2.30-2.25 (m, 1H), 2.06-2.03 (m, 1H); ESI-MS: calc. for $C_{20}H_{18}FN_4O_4[M+H]^+$: 397.4, found: 397.2. ESI-HRMS: calc. for $C_{20}H_{18}FN_4O_4[M+H]^+$: 397.1307, found: 397.1302. HPLC purity: 100% (254 nm), $t_R$: 5.24 min; 100% (220 nm), $t_R$: 5.24 min.

Figure 2:
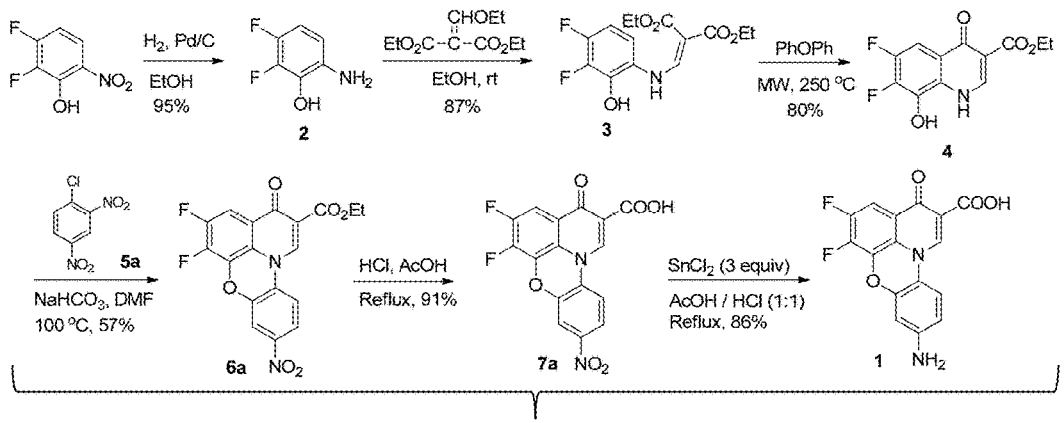
FIG. 2. Scheme 1. Synthesis of 9-amino-5, 6-difluoro-3-oxo-3H-pyrido[3,2,1-kl]phenoxazine-2-carboxylic acid (1).
Figure 3:
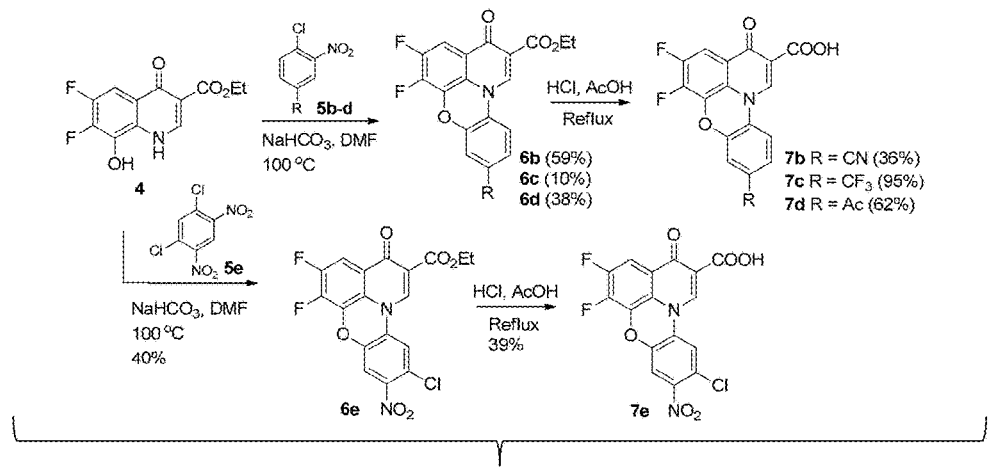
FIG. 3. Scheme 2. Synthesis of fluoroquinophenoxazine derivatives 7b-e.
Figure 4:
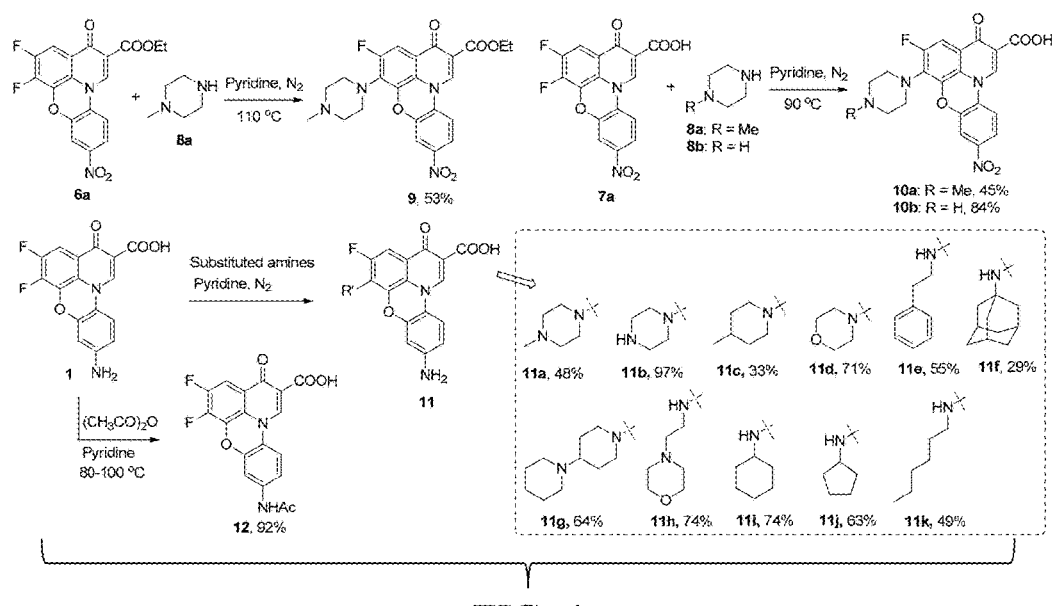
FIG. 4. Scheme 3. Synthesis of diverse amino-substituted fluoroquinophenoxazines 9-11 and acetyl-protected quinophenoxazine 12.

Example 2—Validation of the Chemistry 9-amino-5, 6-difluoro-3-oxo-3H-pyrido[3,2,1-kl]phenoxazine-2-carboxylic acid (1) was synthesized and its biochemical activity tested against *E. coli* topoisomerase I. Resynthesized fluoroquinophenoxazine hit 1 showed reproducible topoisomerase I inhibitory activity with an $IC_{50}$ of 1.95 μM. The synthesis of 1 is shown in Scheme 1 (FIG. 2).

Briefly, commercially available 2,3-difluoro-6-nitrophenol was hydrogenated using Pd/C (20 mol %) as the catalyst to the corresponding amino product 2, which can be used in next step without further purification. Subsequent reaction of the aniline derivative 2 with diethyl 2-(ethoxymethylene) malonate under ambient temperature gave 3 in 87% yield. For next nucleophilic displacement cyclization, an improved protocol was developed for this intramolecular cyclization reaction under microwave irradiation at 250° C. instead of conventional heating [30].

Following simple filtration, 4 was obtained in 80% yield. Subsequently, 4 reacted with 1-chloro-2,4-dinitrobenzene (5a) in DMF at 100° C. to give the desired tetracyclic product 6a in 57% yield. Upon treatment of 6a in acidic condition (AcOH/HCl) under reflux for 4 h, the free carboxylic acid derivative 7a was obtained by simple filtration in 91% yield. Finally, hydrogenation of 7a under $H_2$ (1.0 bar) using $FeSO_4 \cdot 6H_2O$ as the catalyst failed to yield the amine product 1 after 14 h. However, when $SnCl_2$ was used as catalyst and AcOH as the solvent, the nitro group was smoothly reduced into the amino group under reflux for 3 h and the final product 1 was obtained in 86% yield.

Under the optimized conditions, the structural diversity of 1 was expended to evaluate the effect of various substituents on the quinophenoxazine skeleton and to explore their structure-activity relationship (SAR). First, we used various substrates 5b-e in Scheme 2 in an effort to generate a focused set of quinophenoxazine derivatives 7b-e. It is worthwhile noting that a dramatic difference was observed in terms of the reactivity of the substrate 5 with different electronic and/or physiochemical properties. For example, 5b bearing an electron-withdrawing nitrile group facilitated the completion of cyclization in 2 h and 6b was obtained in 59% yield. On the other hand, 5c with the lipophilic trifluoromethyl group could finish the reaction by extending the reaction time, affording the desired product 6c in a lower yield (10%). In addition, when the substrate 5d with an acetyl group was tried, 6d was obtained in 38% yield. However, for the substrate with the corresponding fluorine substitution, no reaction occurred even when the reaction temperature was raised to 120° C. Furthermore, more harsh conditions were tried in an attempt to facilitate the reaction by heating the reaction to 160° C. in a sealed pressure tube or heating the reaction to 200° C. under microwave irradiation, but with not much success. In the case of 5e with additional nitro and chlorine substituents, the reaction proceeded smoothly and 6e was obtained in 40% yield. Final ester hydrolysis was performed in acetic acid/hydrochloric acid under reflux, affording free carboxylic acid products 7b-e in 36-95% yields.

In the course of antibacterial evaluation, compound 1 lost 2-4 fold whole cell antibacterial activity after 4 weeks of storage, indicating that 1 may have stability and/or solubility issues. From $^1$H NMR experiments, it was noted that 1 could be easily precipitated out in $d_6$-DMSO solvent and no degradation-related evidence was observed following several weeks of monitoring 1 in both $d_6$-DMSO NMR and HPLC experiments (data not shown). Thus, to enhance the overall solubility profile of this class of quinophenoxazine derivatives, a variety of solubilizing and polar groups were introduced into the fluoroquinophenoxazine scaffold by displacing the 6-fluorine atom of 6a, 7a, or 1 with different amine functionalities such as piperazine, 1-methylpiperazine, and morpholine (Scheme 3).

Specifically, 6a reacted with 1-methylpiperazine in pyridine at 110° C. to give 9 in 53% yield. Accordingly, 7a reacted with 1-methylpiperazine and piperazine in pyridine under nitrogen atmosphere at 90° C., and both reactions proceeded smoothly to afford 10a and 10b in 45% and 84% yields, respectively [31].

In the cases of 1 and some other amine substrates, notably, reaction temperature appeared to play a critical role in this nucleophilic displacement reaction. For example, when morpholine was used as a nucleophile, the reaction became complicated under 90° C., which is suitable for 1-methylpiperazine and piperazine. In contrast, when temperature was reduced to 70° C., the reaction could be completed in 16 h to produce 11d in 71% yield. Other functional amines were also subjected to this substitution reaction, and most of the reactions could lead to the desired products 11c-k under 90° C. in moderate yields except for 1-adamantylamine.

The reaction of 1 with 1-adamantylamine could finish under reflux after 4 days in 29% yield, presumably due to steric effect. In addition, to investigate the effect of the free amine functionality of 1 on topoisomerase inhibition and antibacterial activity, we next tried to protect the free amino group with acetyl functionality. The N-acetyl derivative 12 was synthesized from 1 and acetic anhydride in pyridine at 80-100° C. and the solid product was collected by simple filtration in high yield (92%).

Finally, to evaluate the potential stereospecific effect at the 6 position of fluoroquinophenoxazine derivatives on biological activity, we designed and synthesized several chiral fluoroquinophenoxazine amine derivatives from 6a or 1 and chiral amine building blocks [31, 32_ENREF_13]._ENREF_6 The nucleophilic substitution reaction of 1 and (S)-3-(Boc-amino)pyrrolidine (13a) in pyridine was completed in 20 h, affording 15a in 86% yield. Subsequent N-Boc deprotection of 15a produced 17a in 78% yield upon the treatment with diluted hydrochloric acid. With regard to the reaction of 1 and the corresponding (R)-3-(Boc-amino)pyrrolidine (13b), the substituted compound 15b could not be obtained by filtration upon the completion of reaction. Therefore, the crude product 15b was used for the following deprotection reaction and the corresponding fluorophenoxazine derivative 17b (R) was obtained in 48% yield over two steps. Accordingly, compound 16 was synthesized from 6a as the starting material in 32% yield over two steps (Scheme 4).

Example 3—Inhibition of *E. coli* Topoisomerase I Relaxation Activity

Recombinant *E. coli* topoisomerase I and gyrase expressed in *E. coli* were purified as described previously [36, 37].

All the synthesized target molecules were tested for the ability to inhibit the relaxation activity of *E. coli* topoisomerase I in target-based assay, as well as against a panel of bacterial strains including the wild-type *E. coli* MG1655 K12 strain, *E. coli* strain BAS3023 with imp mutation conferring membrane permeability to small molecules [38, 39], the wild-type Gram-positive *B. subtilis* (ATCC 6633) strain, and *M. tuberculosis* ($H_{37}$Rv). The results are summarized in Table 1.

*E. coli* Topoisomerase I Relaxation Activity Inhibition Assay

The relaxation activity of *E. coli* topoisomerase I was assayed in a buffer containing 10 mM Tris-HCl, pH 8.0, 50 mM NaCl, 0.1 mg/mL gelatin, and 0.5 mM $MgCl_2$. Half microliter from the appropriate stock solutions of compounds dissolved in the solvent (DMSO) or the solvent alone (control) was mixed with 9.5 µL of the reaction buffer containing 10 ng of enzyme before the addition of 10 µL of reaction buffer containing 200 ng of supercoiled pBAD/Thio plasmid DNA purified by cesium chloride gradient as substrate. Following incubation at 37° C. for 30 min, the reactions were terminated by the addition of 4 µL of a stop buffer (50% glycerol, 50 mM EDTA, and 0.5% (v/v) bromophenol blue), and analyzed by agarose gel electrophoresis. The gels were stained in ethidium bromide and photographed under UV light.

*E. coli* Topoisomerase I Inhibition

Biochemical evaluation for inhibition of the relaxation activity of *E. coli* topoisomerase I revealed that the majority of our synthesized compounds possessed good activity against *E. coli* topoisomerase I. On the basis of these topoisomerase I inhibition data (Table 1), The 9 position substituent plays a very important role in topoisomerase I inhibitory activity. Among the 5,6-difluoroquinophenoxazine derivatives, the hit compound 1 with the electron-donating 9-$NH_2$ group showed the most potent activity ($IC_{50}$=1.95 µM) against *E. coli* topoisomerase I. Both free carboxylic acid 7c and its ethyl ester derivative 6c with the 9-$CF_3$ functionality were inactive against topoisomerase I when tested at 125 µM. In addition, compared to 1 (9-$NH_2$, 1.95 µM), all the other 5,6-difluoro derivatives with 9-substituted electron-withdrawing groups (7a with 9-$NO_2$, 15.6 µM; 7b with 9-CN, 31.25 µM; 7d with 9-Ac, 15.6 µM; 7e with 9-$NO_2$ and 10-Cl, 31.25 µM) were 8-16 fold less active with $IC_{50}$ values ranging from 15.6-31.25 µM. Thus, the topoisomerase I inhibitory activity among these derivative is 1>7a, 7d>7b, 7e.

Figure 6A:
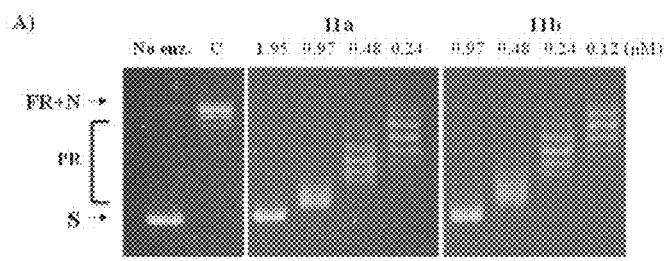
FIGS. 6A-6B. Inhibition of E. coli topoisomerase relaxation activity by representative 11a and 11b. A) E. coli topoisomerase I inhibition assays with supercoiled plasmid DNA. B) E. coli DNA gyrase inhibition assays with relaxed plasmid DNA. C refers to DMSO control; Nor refers to Norfloxacin (125 μM) control; S refers to supercoiled plasmid DNA; N refers to Nicked DNA; FR refers to fully relaxed DNA; PR refers to partially relaxed DNA.
Figure 6B:
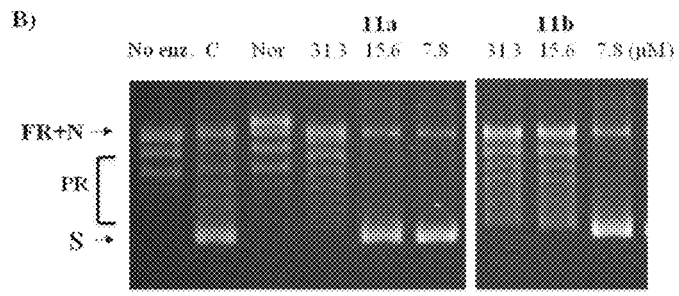

In general, the basic amine functionality at the 6 position significantly enhanced topoisomerase I inhibitory activity. For example, the 6-substituted amine derivatives 11a with 6-methylpiperazinyl, 11b with piperazinyl, 11d with morpholino, 11g with bipiperidinyl, 11h with morpholinoethyl, as well as the 6-substituted aminopyrrolidinyl derivatives 16, 17a, and 17b demonstrated the most potent topoisomerase I inhibitory activity with $IC_{50}$ values of 0.24-0.97 µM; and within this group, 11d and 11h with the morpholino group had an $IC_{50}$ value of 0.97 µM. In contrast, all the other 6-substituted amine derivatives with a more lipophilic side chain, including 11c with methylpiperidinyl, 11e with phenethyl, 11f with adamantanyl, 11i with cyclohexyl, 11j with cyclopentyl, 11k with n-hexyl, and 15a with t-Boc-aminopyrrolidinyl, showed weaker topoisomerase I inhibition with $IC_{50}$ values ranging from 3.9 to 15.6 µM. Notably, both 6-substituted aminopyrrolidinyl S- and R-stereoisomers 17a and 17b exhibited the same topoisomerase I inhibitory activity ($IC_{50}$=0.48-0.97 µM), suggesting the stereochemistry at the 6 position is not required for topoisomerase I inhibition, iii) Esterification of the carboxylic acid group had little effect on the *E. coli* topoisomerase I inhibitory activity by comparing 6a and 7a ($IC_{50}$=15.6 µM), 6b and 7b ($IC_{50}$=31.25 µM), as well as 6c and 7c ($IC_{50}$>125 µM), indicating the ethyl ester functionality is tolerated for topoisomerase I enzyme inhibition. Representative inhibition results of 11a and 11b against *E. coli* topoisomerase relaxation activity are shown in FIG. 6.

TABLE 1

E. coli topoisomerase I inhibition and whole cell antibacterial activities (μM) of fluoroquinophenoxazine derivatives[a]

| Compd | Topoisomerase inhibitory activity (IC$_{50}$, μM) | | | | Whole cell based antibacterial activity (MIC, μM) | | | | | |
|---|---|---|---|---|---|---|---|---|---|---|
| | E. coli topo I (type IA) | E. coli DNA gyrase (type IIA) | Human topo I (type IB) | Human topo IIα (type IIA) | E. coli Imp4213 (BAS3023) | E. coli (MG1655) WT | B. subtilis (ATCC 6633) WT | M. tuberculosis (H$_{37}$Rv) | Vero cell IC$_{50}$ | SI[b] |
| 1 | 1.95 | >125 | 31.3 | >500 | 0.78-1.56 | >200 | 6.25 | 11.2 | 75.7 | 6.8 |
| 6a | 15.6 | | | | 50 | >200 | 25 | | | |
| 6b | 31.25 | | | | >200 | >200 | 200 | | | |
| 6c | >125 | | | | >200 | >200 | >200 | | | |
| 7a | 15.6 | | | | 0.78 | 200 | 12.5 | | | |
| 7b | 31.25 | | | | 200 | >200 | >200 | | | |
| 7c | >125 | | | | >200 | >200 | 25 | | | |
| 7d | 15.6 | | | | >200 | >200 | >200 | | | |
| 7e | 31.25 | 62.5 | 31.25 | 125 | 0.39 | 50 | 3.12 | 29 | >127 | >4.4 |
| 9 | 1.95 | | | | 25 | >200 | 50 | | | |
| 10a | 1.95 | 62.5-125 | 31.25 | 250-500 | 1.56 | 100 | 0.78 | 19 | 95 | 5.0 |
| 10b | 3.9 | | | | >200 | >200 | >200 | | | |
| 11a | 0.48 | 15.6-31.25 | 15.6 | 3.9-7.8 | 0.78 | 6.25 | 0.78 | 7.6 | 29 | 3.8 |
| 11b | 0.24 | 7.8-15.6 | 7.8 | 1.95-3.9 | 0.39 | >200 | 25 | 29.5 | >126 | >4.3 |
| 11c | 3.9 | | | | 3.12 | >200 | 0.78 | | | |
| 11d | 0.97 | 7.8 | 15.6 | 15.6 | 0.19-0.39 | >200 | 0.19 | 3.5 | 24.7 | 7.1 |
| 11e | 3.9 | | | | 50 | >200 | 25-50 | 21.6 | | |
| 11f | 3.9-7.8 | | | | 3.12 | >200 | 12.5 | 38.4 | 30.7 | 0.8 |
| 11g | 0.48 | 15.6 | 3.9 | 1.95-3.9 | 0.39-0.78 | >200 | 1.56 | 2.5 | 24.4 | 9.8 |
| 11h | 0.97 | 15.6-31.25 | 7.8-15.6 | 3.9-7.8 | 0.78 | >200 | 1.56 | 21.6 | 43.0 | 2.0 |
| 11i | 3.9 | | | | 25 | >200 | 12.5 | | | |
| 11j | 3.9 | | | | 25 | >200 | 12.5 | | | |
| 11k | 15.6 | | | | >200 | >200 | >200 | | | |
| 12 | 7.8 | | | | >200 | >200 | >200 | | | |
| 15a | 3.9 | | | | 12.5 | >200 | 12.5 | | | |
| 16 | 0.48 | 3.9 | 7.8 | 1.95-3.9 | 1.56 | >200 | 0.78 | >50 | >50 | |
| 17a | 0.48-0.97 | 3.9 | 3.9 | 0.97-195 | 1.56 | >200 | 6.25 | >63.1 | >63.1 | |
| 17b | 0.48-0.97 | 3.9 | 3.9 | 3.9 | 6.25 | >200 | 12.5 | >63.1 | >63.1 | |

[a]Blank cells indicate Not Determined.
[b]Selectivity index = cytotoxic IC$_{50}$ against Vero cells/MIC against M. tuberculosis.

Example 4— Selectivity and Specificity Against Other DNA Topoisomerase Enzymes

DNA Gyrase Supercoiling Inhibition Assay

DNA gyrase supercoiling assays were carried out by mixing the compounds and the enzyme in a similar manner as above (EcTopI relaxation inhibition assay) but in a gyrase assay buffer (35 mM Tris-HCl, 24 mM KCl, 4 mM MgCl$_2$, 2 mM DTT, 1.75 mM ATP, 5 mM spermidine, 0.1 mg/mL BSA, 6.5% glycerol at pH 7.5), followed by the addition of 300 ng of relaxed covalently closed circular DNA (New England Biolabs, Ipswich, Mass., USA) to a final reaction volume of 20 μL. The samples were incubated at 37° C. for 30 minutes before being terminated by the addition of a buffer containing 5% SDS, 0.25% bromophenol blue, and 25% glycerol. The reactions were then analyzed by agarose gel electrophoresis.

Human Topoisomerase I Relaxation Inhibition Assay

Human topoisomerase I relaxation assays were carried out with 0.5 U of enzyme in reaction buffer supplied by the manufacturer. The enzyme was mixed with the indicated concentration of compound dissolved before 200 ng of supercoiled pBAD/Thio plasmid DNA was added in the same buffer, for a final volume of 20 μL. Following incubation at 37° C. for 30 minutes, the reactions were terminated with a buffer containing 5% SDS, 0.25% bromophenol blue, and 25% glycerol, and analyzed by agarose gel electrophoresis.

Human topoisomerase I and topoisomerase IIα were purchased from TopoGen (Buena vista, CO, USA).

Human Topoisomerase IIα Decatenation Inhibition Assay

Human Topoisomerase IIα assays were carried out by adding the compounds to 185 ng of kinetoplast DNA (kDNA, from TopoGen) in the buffer supplied by the manufacturer before the addition of 2 U of the enzyme. The samples were incubated for 15 minutes at 37° C. before the addition of 4 μL of a stop buffer containing 5% sarkosyl, 0.25% bromophenol blue, and 25% glycerol. The reactions were then analyzed by electrophoresis in 1% agarose gels containing 0.5 g/mL ethidium bromide before being photographed under UV light.

Selectivity and Specificity Against Other DNA Topoisomerase Enzymes

In addition, to determine the selectivity and specificity profiles of this class of fluoroquinophenoxazine derivatives, selected compounds were also investigated for the ability to inhibit other DNA topoisomerases including E. coli DNA gyrase as well as human topoisomerase I and IIα enzymes.

Overall, these compounds were more selective toward E. coli topoisomerase I than other enzymes tested. Given that this series of compounds has close structural similarity to quinolone antibiotic class, as such, inhibition against E. coli gyrase can be also observed. Specifically, most of the compounds showed 4-64 fold selectivity toward topoisomerase I over DNA gyrase except that the moderately active compound 7e with the 9-NO$_2$ and 10-chloro substituents showed less specificity with 2 fold selectivity toward topoisomerase I. With respect to human topoisomerases I and IIα inhibition, these compounds also showed inhibitory activity against both human topoisomerase I (IC$_{50}$=3.9-

31.25 µM) and topoisomerase IIα (IC$_{50}$=0.97-250 µM), with approximate 4-32 fold selectivity. Taken together, compounds 11a (IC$_{50}$=0.48 µM) and 11b (IC$_{50}$=0.24 µM) (FIG. 6) bearing both 9-NH$_2$ and 6-piperazinyl motifs exhibited the most potent topoisomerase I inhibitory activity with the more favorable selectivity profile (8-64 fold) toward *E. coli* topoisomerase I against all the other enzymes tested.

Example 5—Cell-Based Assays

The minimum inhibitory concentrations (MIC) of the compounds were determined against *E. coli* and *B. subtilis* in cation-adjusted Mueller-Hinton Broth according to standard microdilution protocol [40].

MICs of compounds against *M. tuberculosis* were determined by a modified microplate Alamar blue assay (MABA) [41]. Vero cell cytotoxicity assay was performed as previously described [41].

Cell-Based Antibacterial Activity

In addition to target-based topoisomerase enzyme inhibition, whole cell antibacterial activities of the synthesized compounds were also assessed against a panel of bacterial strains. The results are also shown in Table 1. From these data, the majority of these fluoroquinophenoxazine derivatives exhibited good to excellent antibacterial activity against the membrane permeable *E. coli* strain BAS3023 and Gram-positive *B. subtilis* strain, and were inactive against the wide type *E. coli* strain. Additionally, the antibacterial activity of most fluoroquinophenoxazine derivatives (e.g., 1, 7a, 7c, 9, 10a, 11a-d, 11f-i, 15a, 16, and 17a-b) generally correlated with *E. coli* topoisomerase I inhibitory activity, suggesting that the antibacterial basis of these compounds may be in part due to the inhibition of topoisomerase I. The only type IA topoisomerase present in *M. tuberculosis* has recently been validated as an antitubercular target [42]. The topoisomerase I activity has been shown to be essential for viability and infection in a murine model of tuberculosis [42, 43]. To further determine the antituberculosis profile for this chemical class of fluoroquinophenoxazine derivatives, twelve compounds were selected and evaluated against *M. tuberculosis*. Among them, 11g with the 6-bipiperidinyl lipophilic side chain and 11d with the 6-morpholino heterocyclic ring system showed the most potent antituberculosis activity with minimum inhibitory concentration (MIC) values of 2.5 and 3.5 µM, respectively. In addition, compared to 11d, its corresponding 6-piperazinyl structural analogs 11a with tertiary amine and 11b with secondary amine functionality was about 2- and 8-fold less active with the MIC values of 7.6 and 29.5 µM, respectively. In contrast, both 6-substituted aminopyrrolidinyl derivatives 17a (S) and 17b (R) with primary amine functionality were not active (MIC>63.1 µM) against *M. tuberculosis*.

These data strongly suggest that the decreased or lost whole cell antituberculosis activity of these compounds are most likely due to their decreased lipophilicity and subsequent cell membrane penetration. Unfortunately, cytotoxicity evaluation of our tested compounds against healthy normal Vero cells showed that they generally had narrow selectivity index, with 11g (SI=9.8) being the most promising compound. It is also worthwhile noting that, one of the most potent topoisomerase I inhibitors, 11a (IC$_{50}$=0.48 µM) bearing the 6-methylpiperazinyl and 9-amino motifs, showed broad spectrum antibacterial activity against all the test bacteria strains with MICs ranging from 0.78 to 7.6 µM (SI=3.8-37).

TABLE 2

IC50 (µM) of compounds 11d, 11e, and 11g against *Mycobacterium tuberculosis* topoisomerase I and MIC (µM) values of compounds 11d, 11e, and 11g for TB (*Mycobacterium tuberculosis* strain H37Rv) and MRSA (*staphylococcus aureus* BAA44).

| Code | Structure | IC50 | MIC (TB) | MIC (MRSA) |
|---|---|---|---|---|
| 11d | 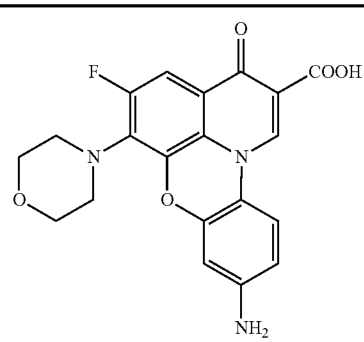 | 0.48 | To be determined | 3 |
| 11g | 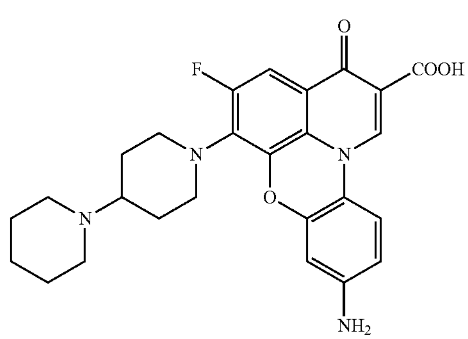 [SMILES: Nc1ccc2c(c1)Oc1c(N3CCC(N4CCCCC4)CC3)c(F)cc3c(=O)c(C(=O)O)cn-2c13] | 0.24 | 2.5 | 12.5 |

TABLE 2-continued

IC50 (µM) of compounds 11d, 11e, and 11g against *Mycobacterium tuberculosis* topoisomerase I and MIC (µM) values of compounds 11d, 11e, and 11g for TB (*Mycobacterium tuberculosis* strain H37Rv) and MRSA (*staphylococcus aureus* BAA44).

| Code | Structure | IC50 | MIC (TB) | MIC (MRSA) |
|---|---|---|---|---|
| 11e | [structure] | 0.24 | 21.6 | 25 |

Viability of the mycobacteria *mycobacterium smegmatis* in biofilm was measured by the resazurin assay. Compound 11g at 1.5-3 µM can abolish 90% of viability, versus 24 µM or higher required for ciprofloxacin to achieve the same anti-biofilm activity.

The resazurin assay is a quick method using the resazurin dye as a bacterial respiration indicator to assay the antibacterial activity of various compounds used against bacterial biofilm growth. Such assay is well-known in the art. Resazurin was used to measure the presence of active biofilm bacteria, after adding the compound, in relation to a standard curve generated from inocula in suspension of the same organism used to grow the biofilm. The biofilm was quantified indirectly by measuring the fluorescent, water-soluble resorufin product produced when resazurin is reduced by reactions associated with respiration.

Example 6—CoMFA Modeling

Dataset

All the synthesized and tested fluoroquinophenoxazine derivatives were used for CoMFA study. The topoisomerase I inhibitory activity ($IC_{50}$, µM) from biochemical enzyme assay was converted to $pIC_{50}$ values for correlation purpose ($pIC_{50}$=-log $IC_{50}$). The total compound set is divided into two subsets: a training set of 21 compounds for generating 3D-quantitative structure-activity relationship (QSAR) models and a test set of 7 compounds for validating the quality of the model (Table 3). The compound selections of training and test sets were done manually so that compounds ranging from weak, moderate, to strong topoisomerase I inhibitory activities were present in both sets and were in approximately equal proportions.

Conformational Model Analysis and Molecular Alignment

In the 3D-QSAR studies, alignment rule and biological conformation selection are two important factors to construct reliable models. For both training and test set molecules, conformational models representing their available conformational space were calculated. All the molecules were subjected to produce a maximum of 255 conformations within 20 kcal/mol in energy from global minimum. Due to the relatively rigid structural feature of these molecules, the core structure of quinophenoxazine was used for the alignment.

CoMFA Model Generation

CoMFA was performed using the QSAR module of SYBYL-X [44]. The steric and electrostatic field energies were calculated using the Lennard-Jones and the Coulomb potentials, respectively, with a 1/r distance-dependent dielectric constant in all intersections of a regularly spaced (0.2 nm) grid. The electrostatic fields were computed using Gasteiger-Huckel charge calculation methods. A $sp^3$ hybridized carbon atom with a radius of 1.53 Å and a charge of +1.0 was used as a probe to calculate the steric and electrostatic energies between the probe and the molecules using the Tripos force field. The standard parameters implemented in SYBYL-X were used. The truncation for both steric and electrostatic energies was set to 30 kcal/mol.

Partial Least Square (PLS) Analysis

PLS methodology [45] was used for 3D-QSAR analysis. The cross-validation analysis [46, 47] was performed using the leave one out (LOO) methods in which one compound is removed from the dataset and its activity is then predicted using the model derived from the rest of the dataset. The cross validated $r^2$ that resulted in the optimum number of components and the lowest standard error of prediction were considered for further analysis. To speed up the analysis and reduce noise, a minimum filter value of 2.00 kcal/mol was used. A final analysis was performed to calculate conventional $r^2$ using the optimum number of components obtained from the cross-validation analysis.

CoMFA Analysis

Figure 7:
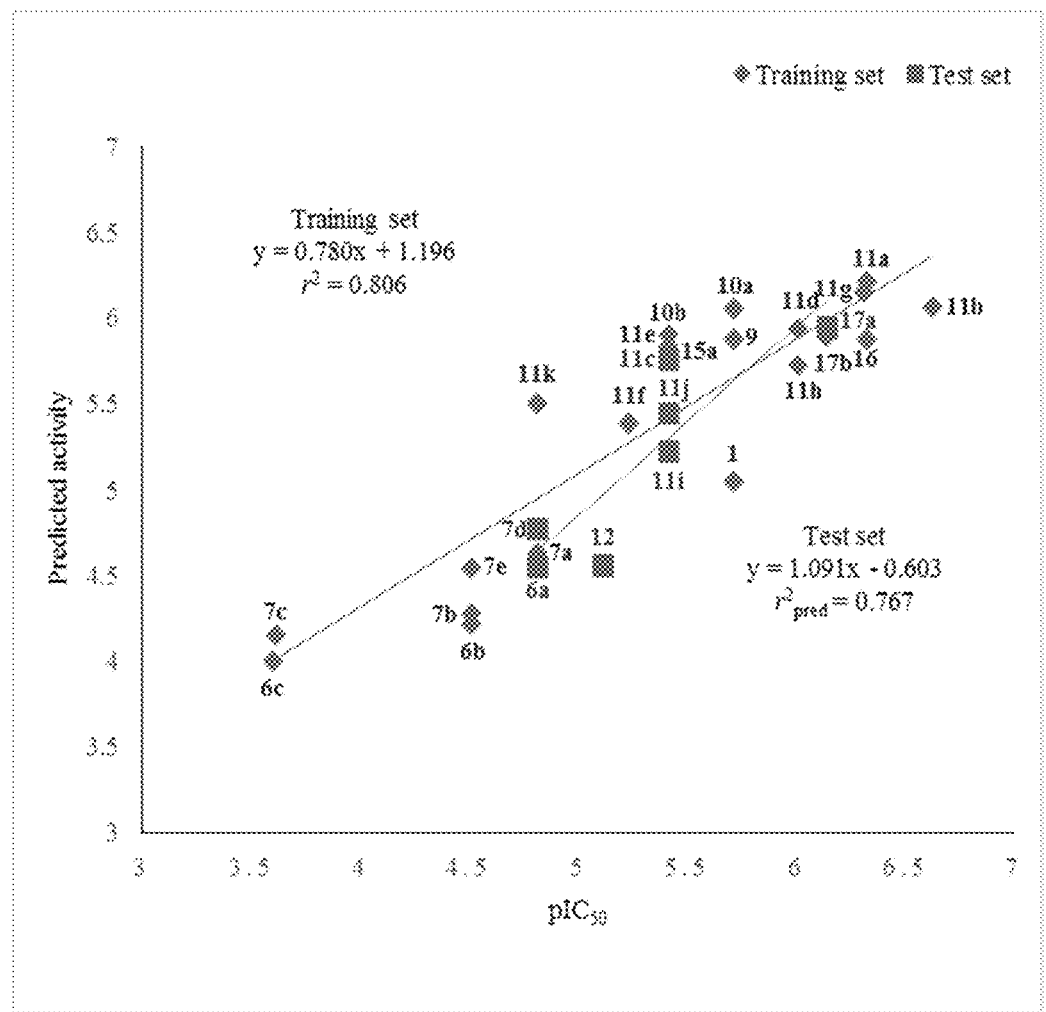
FIG. 7. The correlation chart of experimental versus predicted values for the training and test set compounds.

To further understand the structural basis for topoisomerase I inhibitory activity of this set of fluoroquinophenoxazine derivatives, we subsequently performed three dimensional QSAR (3D-QSAR) study using CoMFA analysis [48_ENREF_23]. Because of the relatively rigid core structural feature of this class of fluoroquinophenoxazine molecules, we directly applied core structure based alignment to build reliable 3D-QSAR models. The CoMFA study was carried out using a total of 21 compounds (entries 1-21, Table 3). Statistical parameters of the CoMFA model showed a reasonable cross-validated correlation coefficient $q^2$ of 0.688, indicating a good internal prediction of the model. The CoMFA model also exhibited a conventional correlation coefficient $r^2$ of 0.806. To evaluate the predictive ability of our developed model, a test set of 7 compounds (entries 22-28, Table 3) which was not included in model generation was subsequently used. The predicative correlation coefficient $r^2_{pred}$ of 0.767 indicates good external predicative ability of the CoMFA model. The experimental and predicted values as well as their residuals from the training and test set molecules are listed in Table 3. The correlation between the predicted and experimental values of all compounds was plotted and the resulting chart is shown in FIG. 7.

TABLE 3

Experimental (pIC$_{50}$) and CoMFA predicted activity (PA) values and residuals for the training and test set compounds$^a$

| Entry | Compd. | IC$_{50}$ (µM) | PIC$_{50}$ | CoMFA PA$^b$ | Δ$^c$ |
|---|---|---|---|---|---|
| 1 | 1 | 1.95 | 5.71 | 5.05 | 0.66 |
| 2 | 6b | 31.25 | 4.51 | 4.21 | 0.30 |
| 3 | 6c | 250 | 3.60 | 4.00 | −0.40 |
| 4 | 7a | 15.6 | 4.81 | 4.63 | 0.18 |
| 5 | 7b | 31.25 | 4.51 | 4.27 | 0.24 |
| 6 | 7c | 250 | 3.61 | 4.15 | −0.54 |
| 7 | 7e | 31.25 | 4.51 | 4.54 | −0.03 |
| 8 | 9 | 1.95 | 5.71 | 5.88 | −0.17 |
| 9 | 10a | 1.95 | 5.71 | 6.05 | −0.34 |
| 10 | 10b | 3.9 | 5.41 | 5.90 | −0.49 |
| 11 | 11a | 0.48 | 6.32 | 6.21 | 0.11 |
| 12 | 11b | 0.24 | 6.62 | 6.06 | 0.56 |
| 13 | 11d | 0.97 | 6.01 | 5.94 | 0.07 |
| 14 | 11e | 3.9 | 5.41 | 5.83 | −0.42 |
| 15 | 11f | 5.85 | 5.23 | 5.39 | −0.16 |
| 16 | 11g | 0.48 | 6.31 | 6.15 | 0.16 |
| 17 | 11h | 0.97 | 6.01 | 5.72 | 0.29 |
| 18 | 11k | 15.6 | 4.81 | 5.50 | −0.69 |
| 19 | 15a | 3.9 | 5.41 | 5.77 | −0.36 |
| 20 | 16 | 0.48 | 6.32 | 5.88 | 0.44 |
| 21 | 17b | 0.73 | 6.14 | 5.89 | 0.25 |
| 22 | 6a | 15.6 | 4.81 | 4.55 | 0.26 |
| 23 | 7d | 15.6 | 4.81 | 4.77 | 0.04 |
| 24 | 11c | 3.9 | 5.41 | 5.76 | −0.35 |
| 25 | 11i | 3.9 | 5.41 | 5.23 | 0.18 |
| 26 | 11j | 3.9 | 5.41 | 5.45 | −0.04 |
| 27 | 12 | 7.8 | 5.11 | 4.56 | 0.55 |
| 28 | 17a | 0.73 | 6.14 | 5.95 | 0.19 |

$^a$Entries 1-21 for training set; entries 22-28 for test set.
$^b$Predicted activity.
$^c$Residual of experimental and predicted activity values.

Figure 5:
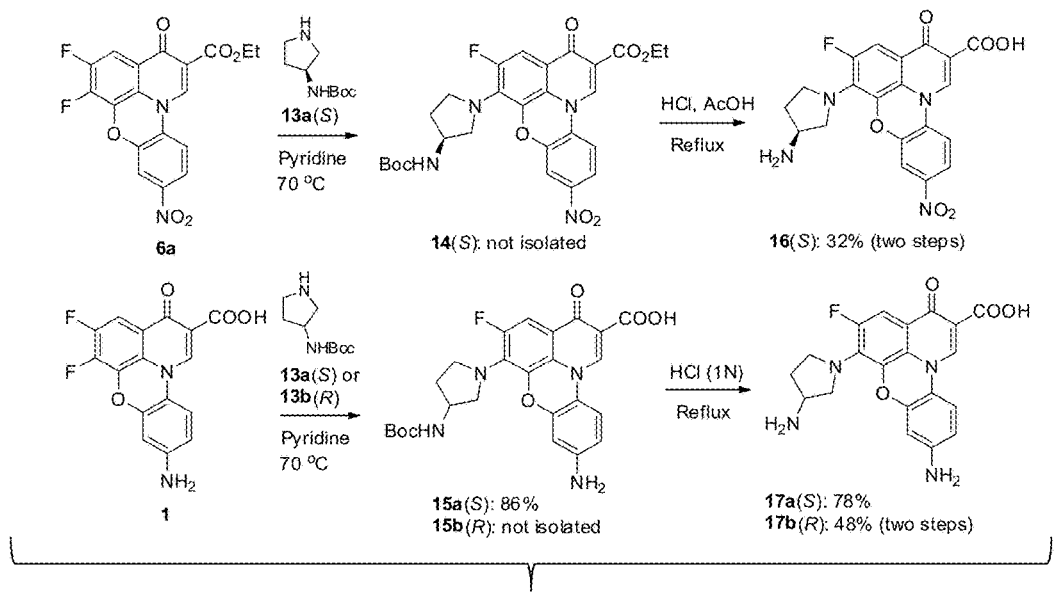
FIG. 5. Scheme 4. Synthesis of fluoroquinophenoxazine chiral amine derivatives 16 and 17.

The results of the CoMFA model were analyzed and visualized using the standard deviation coefficient (StDev*Coeff) mapping option contoured by steric and electrostatic contributions. In order to probe the structure/activity correlation, the steric and electrostatic contours were mapped onto their aligned chemical structures of these fluoroquinophenoxazine molecules to identify the potential regions in which the molecules would favorably or unfavorably interact with the topoisomerase I enzyme. The representative steric and electrostatic contour maps of the most active compound 11b and the least active 6c derived from the CoMFA model are shown in FIG. 5. Briefly, the yellow areas in the steric contour maps indicate regions of steric hindrance to activity, while the green areas indicating steric contribution to potency. From the electrostatic contour maps, the regions in blue indicate positive electrostatic charge potential associated with increased activity, with the red regions show electronegative groups with increased activity.

Figure 8A:
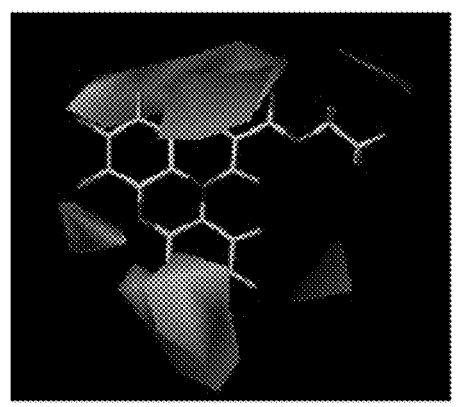
FIGS. 8A-8D. Representative CoMFA steric and electrostatic contour maps. A). Steric contour maps with 6c; B). Steric contour maps with 11b; C). Electrostatic contour maps with 6c; and D) Electrostatic contour maps with 11b.
Figure 8B:
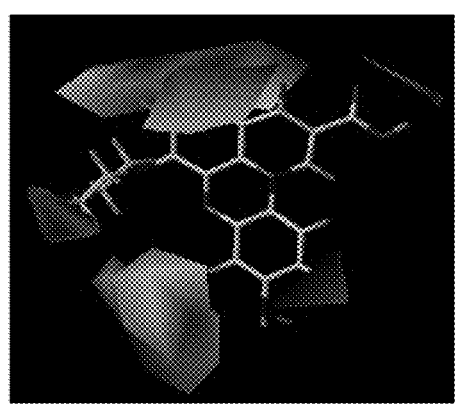

In FIG. 8A and FIG. 8B, one green contour was found near the piperazinyl moiety of compound 11b indicating that a moderate steric substituent would be favored at the 6 position of the quinophenoxazine scaffold. This may offer a potential explanation why the 6-substituted amino derivatives were generally more active than the 6-fluoro analogs. In addition, two yellow contours were observed near the 9 position of inactive 6c, indicating that a steric bulkiness (e.g., NO$_2$ in 6a and 7a, CF$_3$ in 6c, and the acetyl group in 7d) would be disfavored for activity in this area.

Figure 8C:
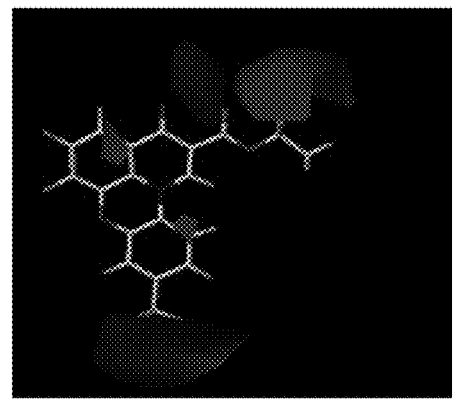
Figure 8D:
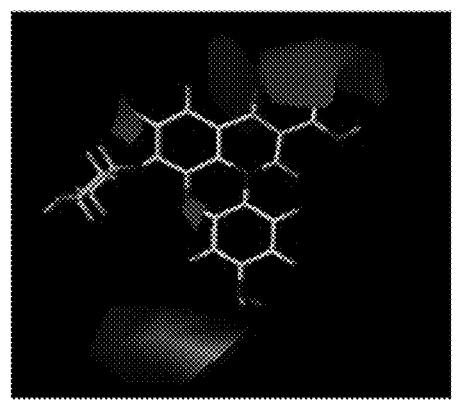

The CoMFA electrostatic contour maps are displayed in FIG. 8C and FIG. 8D. A large blue contour was found around the 9 position of compounds 11b and 6c, indicating that the presence of electron rich functionalities and positively charged environment at this position (e.g., NH$_2$ vs. NO$_2$, Ac, CN, and CF$_3$) would be strongly favored for topoisomerase I inhibitory activity. It was also observed that a big red contour region was present around the 2 position of fluoroquinophenoxazine scaffold, suggesting that an electronegative group (e.g., COOH and COOR$_2$) at this position may be required for activity. Finally, two red contours were found at both sides of the fused heterocyclic skeleton of 11b and 6c, suggesting that electron deficient functionalities would be favored in those regions.

All patents, patent applications, provisional applications, and publications referred to or cited herein are incorporated by reference in their entirety, including all figures and tables, to the extent they are not inconsistent with the explicit teachings of this specification.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Friedman N D, Temkin E, Carmeli Y. 2015. The Negative Impact of Antibiotic Resistance. Clin. Microbiol. Infect. doi: S1198-743X(15)01028-9 [pii].
2. Engstrom A. 2016. Fighting an old disease with modern tools: characteristics and molecular detection methods of drug-resistant *Mycobacterium tuberculosis*. Infect. Dis. (Lond). 48:1-17. doi: 10.3109/23744235.2015.1061205 [doi].
3. Matteelli A, Roggi A, Carvalho A C. 2014. Extensively drug-resistant *tuberculosis*: epidemiology and management. Clin. Epidemiol. 6:111-118. doi: 10.2147/CLEP.S35839 [doi].
4. Chen S H, Chan N L, Hsieh T S. 2013. New mechanistic and functional insights into DNA topoisomerases. Annu. Rev. Biochem. 82:139-170. doi: 10.1146/annurev-biochem-061809-100002; 10.1146/annurev-biochem-061809-100002.
5. Vos S M, Tretter E M, Schmidt B H, Berger J M. 2011. All tangled up: how cells direct, manage and exploit topoisomerase function. Nat. Rev. Mol. Cell Biol. 12:827-841. doi: 10.1038/nrm3228; 10.1038/nrm3228.
6. Schoeffler A J, Berger J M. 2008. DNA topoisomerases: harnessing and constraining energy to govern chromosome topology. Q. Rev. Biophys. 41:41-101. doi: 10.1017/S003358350800468X.
7. Aldred K J, Kerns R J, Osheroff N. 2014. Mechanism of Quinolone Action and Resistance. Biochemistry. doi: 10.1021/bi5000564.
8. Tomasic T, Masic L P. 2014. Prospects for developing new antibacterials targeting bacterial type IIA topoisomerases. Curr. Top. Med. Chem. 14:130-151. doi: CTMC-EPUB-57427 [pii].
9. Tse-Dinh Y C. 2009. Bacterial topoisomerase I as a target for discovery of antibacterial compounds. Nucleic Acids Res. 37:731-737. doi: 10.1093/nar/gkn936.
10. Drlica K. 1992. Control of bacterial DNA supercoiling. Mol. Microbiol. 6:425-433.
11. Masse E, Drolet M. 1999. Relaxation of transcription-induced negative supercoiling is an essential function of Escherichia coli DNA topoisomerase I. J. Biol. Chem. 274:16654-16658.
12. Tse-Dinh Y C. 2015. Targeting bacterial topoisomerase I to meet the challenge of finding new antibiotics. Future Med. Chem. 7:459-471. doi: 10.4155/fmc.14.157 [doi].
13. Zhang Z, Cheng B, Tse-Dinh Y C. 2011. Crystal structure of a covalent intermediate in DNA cleavage and rejoining by Escherichia coli DNA topoisomerase I. Proc. Natl. Acad. Sci. U.S.A. 108:6939-6944. doi: 10.1073/pnas.1100300108.
14. Tan K, Zhou Q, Cheng B, Zhang Z, Joachimiak A, Tse-Dinh Y C. 2015. Structural basis for suppression of hypernegative DNA supercoiling by E. coli topoisomerase I. Nucleic Acids Res. 43:11031-11046. doi: 10.1093/nar/gkv1073 [doi].
15. Yamaguchi Y, Inouye M. 2015. An endogenous protein inhibitor, YjhX (TopAI), for topoisomerase I from Escherichia coli. Nucleic Acids Res. 43:10387-10396. doi: 10.1093/nar/gkv1197 [doi].
16. Yigit H, Reznikoff W S. 1998. Escherichia coli DNA topoisomerase I and suppression of killing by Tn5 transposase overproduction: topoisomerase I modulates Tn5 transposition. J. Bacteriol. 180:5866-5874.
17. Yigit H, Reznikoff W S. 1999. Escherichia coli DNA topoisomerase I copurifies with Tn5 transposase, and Tn5 transposase inhibits topoisomerase I. J. Bacteriol. 181:3185-3192.
18. Pruss G J, Manes S H, Drlica K. 1982. Escherichia coli DNA topoisomerase I mutants: increased supercoiling is corrected by mutations near gyrase genes. Cell. 31:35-42. doi: 0092-8674(82)90402-0 [pii].
19. DiNardo S, Voelkel K A, Sternglanz R, Reynolds A E, Wright A. 1982. Escherichia coli DNA topoisomerase I mutants have compensatory mutations in DNA gyrase genes. Cell. 31:43-51. doi: 0092-8674(82)90403-2 [pii].
20. Garcia M T, Blazquez M A, Ferrandiz M J, Sanz M J, Silva-Martin N, Hermoso J A, de la Campa A G. 2010. New alkaloid antibiotics that target the DNA topoisomerase I of Streptococcus Pneumoniae. J. Biol. Chem. doi: 10.1074/jbc.M110.148148.
21. Suerbaum S, Brauer-Steppkes T, Labigne A, Cameron B, Drlica K. 1998. Topoisomerase I of Helicobacter pylori: juxtaposition with a flagellin gene (flaB) and functional requirement of a fourth zinc finger motif. Gene. 210:151-161.
22. Ahmed W, Menon S, Godbole A A, Karthik P V, Nagaraja V. 2014. Conditional silencing of topoisomerase I gene of Mycobacterium tuberculosis validates its essentiality for cell survival. FEMS Microbiol. Lett. 353:116-123. doi: 10.1111/1574-6968.12412 [doi].
23. Ravishankar S, Ambady A, Awasthy D, Mudugal N V, Menasinakai S, Jatheendranath S, Guptha S, Sharma S, Balakrishnan G, Nandishaiah R, Ramachandran V, Eyermann C J, Reck F, Rudrapatna S, Sambandamurthy V K, Sharma U K. 2015. Genetic and chemical validation identifies Mycobacterium tuberculosis topoisomerase I as an attractive anti-tubercular target. Tuberculosis (Edinb). doi: S1472-9792(15)20742-1 [pii].
24. Godbole A A, Ahmed W, Bhat R S, Bradley E K, Ekins S, Nagaraja V. 2014. Inhibition of Mycobacterium tuberculosis topoisomerase I by m-AMSA, a eukaryotic type II topoisomerase poison. Biochem. Biophys. Res. Commun. 446:916-920. doi: 10.1016/j.bbrc.2014.03.029 [doi].
25. Tang S C, Shapiro T A. 2010. Newly identified antibacterial compounds are topoisomerase poisons in African trypanosomes. Antimicrob. Agents Chemother. 54:620-626. doi: 10.1128/AAC.01025-09.
26. Cheng B, Liu I, Tse-Dinh Y C. 2007. Compounds with antibacterial activity that enhance DNA cleavage by bacterial DNA topoisomerase I. J. Antimicrob. Chemother. 59:640-645.
27. Bansal S, Sinha D, Singh M, Cheng B, Tse-Dinh Y C, Tandon V. 2012. 3,4-dimethoxyphenyl bis-benzimidazole, a novel DNA topoisomerase inhibitor that preferentially targets Escherichia coli topoisomerase I. J. Antimicrob. Chemother. 67:2882-2891. doi: 10.1093/jac/dks322 [doi].
28. Nimesh H, Sur S, Sinha D, Yadav P, Anand P, Bajaj P, Virdi J S, Tandon V. 2014. Synthesis and biological evaluation of novel bisbenzimidazoles as Escherichia coli topoisomerase IA inhibitors and potential antibacterial agents. J. Med. Chem. 57:5238-5257. doi: 10.1021/jm5003028 [doi].
29. Karl, D., Muhammad, M., Fluoroquinolones: Action and resistance, Curr. Top. Med. Chem. 3 (2003) 249-282.
30. Rádl, S., Zikán, V., Synthesis and antimicrobial activity of some 3-oxo-3H-pyrido[3,2,1-kl]phenoxazine-2-carboxylic acids, Collect. Czech. Chem. Commun. 54 (1989) 506-515.
31. Chu, D. T. W., Maleczka, R. E., Synthesis of 4-oxo-4H-quino[2,3,4-ij][1,4]-benoxazine-5-carboxylic acid derivatives, J. Heterocyclic Chem. 24 (1987) 453-456.
32. Kang, D.-H., Kim, J.-S., Jung, M.-J., Lee, E.-S., Jahng, Y., Kwon, Y., Na, Y., New insight for fluoroquinophenoxazine derivatives as possibly new potent topoisomerase I inhibitor, Bioorg. Med. Chem. Lett. 18 (2008) 1520-1524.
33. Permana, P. A., Snapka, R. M., Shen, L. L., Chu, D. T. W., Clement, J J., Plattner, J J., Quinobenoxazines: A class of novel antitumor quinolones and potent mammalian DNA topoisomerase II catalytic inhibitors, Biochemistry 33 (1994) 11333-11339.
34. Fan, J.-Y., Sun, D., Yu, H., Kerwin, S. M., Hurley, L. H., Self-assembly of a quinobenzoxazine-$Mg^{2+}$ complex on DNA: A new paradigm for the structure of a drug-DNA complex and implications for the structure of the quinolone bacterial gyrase-DNA complex, J. Med Chem. 38 (1995) 408-424.
35. Duan, W., Rangan, A., Vankayalapati, H., Kim, M.-Y., Zeng, Q., Sun, D., Han, H., Fedoroff, O. Y., Nishioka, D., Rha, S. Y., Izbicka, E., Von Hoff, D. D., Hurley, L. H., Design and synthesis of fluoroquinophenoxazines that interact with human telomeric G-quadruplexes and their biological effects, Mol. Cancer Ther. 1 (2001) 103-120.

36. Narula, G., Annamalai, T., Aedo, S., Cheng, B., Sorokin, E., Wong, A., Tse-Dinh, Y.-C., The strictly conserved Arg-321 residue in the active site of *Escherichia coli* topoisomerase I plays a critical role in DNA rejoining, *J. Biol. Chem.* 286 (2011) 18673-18680.

37. Hallett, P., Grimshaw, A. J., Wigley, D. B., Maxwell, A., Cloning of the DNA gyrase genes under tac promoter control: overproduction of the gyrase A and B proteins, Gene 93 (1990) 139-142.

38. Sampson, B. A., Misra, R I, Benson, S. A., Identification and characterization of a new gene of *Escherichia coli* K-12 involved in outer membrane permeability, *Genetics* 122 (1989) 491-501.

39. Braun, M., Silhavy, T. J., Imp/OstA is required for cell envelope biogenesis in *Escherichia coli*, *Mol. Microbiol.* 45 (2002) 1289-1302.

40. Andrews, J. M., Determination of minimum inhibitory concentrations, *J. Antimicrob. Chemother.* 48 (2001) 5-16.

41. Falzari, K., Zhu, Z., Pan, D., Liu, H., Hongmanee, P., Franzblau, S. G., In vitro and in vivo activities of macrolide derivatives against *Mycobacterium tuberculosis*, *Antimicrob. Agents Chemother.* 49 (2005) 1447-1454.

42. Ravishankar, S., Ambady, A., Awasthy, D., Mudugal, N. V., Menasinakai, S., Jatheendranath, S., Guptha, S., Sharma, S., Balakrishnan, G., Nandishaiah, R., Ramachandran, V., Eyermann, C. J., Reck, F., Rudrapatna, S., Sambandamurthy, V. K., Sharma, U. K., Genetic and chemical validation identifies *Mycobacterium tuberculosis* topoisomerase I as an attractive antitubercular target, *Tuberculosis* 95 (2015) 589-598.

43. Ahmed, W., Menon, S., Godbole, A. A., Karthik, P. V. D. N. B., Nagaraja, V., Conditional silencing of topoisomerase I gene of *Mycobacterium tuberculosis* validates its essentiality for cell survival, *FEMS Microbiol. Lett.* 353 (2014) 116-123.

44. SYBYL-X/QSAR, Molecular Modelling Software, Tripos International, 1699 South Hanley Rd., St. Louis, Mo., 63144, USA.

45. Masand, V. H., Mahajan, D. T., Alafeefy, A. M., Bukhari, S. N. A., Elsayed, N. N., Optimization of antiproliferative activity of substituted phenyl 4-(2-oxoimidazolidin-1-yl) benzenesulfonates: QSAR and CoMFA analyses, *Eur. J. Pharm. Sci.* 77 (2015) 230-237.

46. Podlogar, B. L., Poda, G. I., Demeter, D. A., Zhang, S. P., Carson, J. R., Neilson, L. A., Reitz, A. B., Ferguson, D. M., Synthesis and evaluation of 4-(N,N-diarylamino) piperidines with high selectivity to the delta-opioid receptor: a combined 3D-QSAR and ligand docking study, *Drug Des. Discov.* 17 (2000) 34-50.

47. Ståhle, L., Wold, S., Partial least squares analysis with cross-validation for the two-class problem: A Monte Carlo study, *J. Chemom.* 1 (1987) 185-196.

48. Cramer, R. D., Patterson, D. E., Bunce, J. D., Comparative molecular field analysis (CoMFA). 1. Effect of shape on binding of steroids to carrier proteins, *J. Am. Chem. Soc.* 110 (1988) 5959-5967.

We claim:

1. A compound having the following structure:

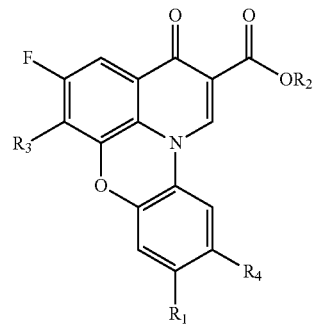

$R_1$ being selected from H, —OH, —$NH_2$, —$NO_2$, —CN, —$CF_3$, alkyl, and substituted alkyl;

$R_2$ being selected from H, alkyl, and substituted alkyl;

$R_3$ being

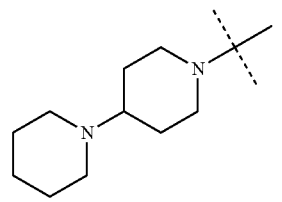

and $R_4$ is selected from H, —OH, —$NH_2$, —$NO_2$, $CF_3$, fluorine, chloride, bromine, iodine, alkyl, and substituted alkyl.

2. A pharmaceutical composition for treating a bacterial infection comprising a compound of claim 1 and a pharmaceutically acceptable carrier.

3. The compound according to claim 1, which has antibacterial activity against a bacterial pathogen, wherein the bacterial pathogen is *M. tuberculosis* or non-*tuberculosis* mycobacteria (NTM).

4. The compound according to claim 1, $R_1$ beingis selected from —$NH_2$, —$NO_2$, —Ac, —CN, and —$CF_3$.

5. A method for treating a bacterial infection in a subject, wherein the method comprises administering, to a subject in need of such treatment, an effective amount of the pharmaceutical composition comprising a compound of claim 1 and a pharmaceutically acceptable carrier.

6. The method according to claim 5, wherein the bacterial infection is caused by a bacterial pathogen selected from *M. tuberculosis* and non-*tuberculosis* mycobacteria (NTM).

7. A method for inhibiting a topoisomerase, wherein the method comprises administering, to a cell, an effective amount of a compound of claim 1.

8. The compound according to claim 1, $R_2$ being H or an ethyl group.

9. The compound according to claim 1, $R_4$ being H or alkyl.

10. The compound according to claim 1, which is:

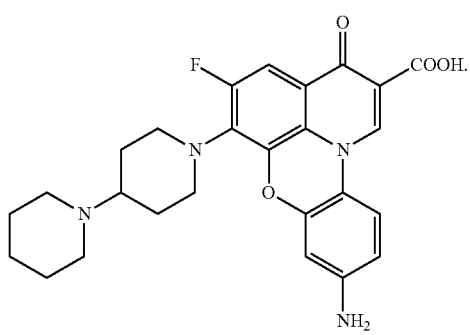

11g

11. A compound having the following structure:

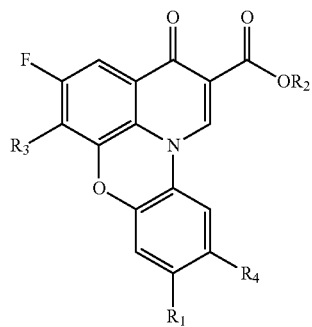

$R_1$ being selected from H, —OH, —$NH_2$, —$NO_2$, —NHMe, —Ac, —CN, —NHAc, —NHCH$_2$CH$_2$NH$_2$, —CF$_3$, fluorine, chloride, bromine, iodine, alkyl, substituted alkyl, aryl, substituted aryl, heteroaryl, substituted heteroaryl, cycloalkyl, substituted cycloalkyl, cycloalkenyl, substituted cycloalkenyl, heterocycloalkyl, and substituted heterocycloalkyl;

$R_2$ being selected from H, alkyl, and substituted alkyl;

$R_3$ being

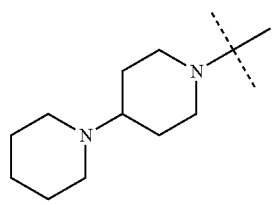

and $R_4$ being selected from H, —OH, —$NH_2$, —$NO_2$, —NHMe, —Ac, —CN, —NHAc, —NHCH$_2$CH$_2$NH$_2$, —CF$_3$, fluorine, chloride, bromine, iodine, alkyl, substituted alkyl, aryl, substituted aryl, heteroaryl, substituted heteroaryl, cycloalkyl, substituted cycloalkyl, cycloalkenyl, substituted cycloalkenyl, heterocycloalkyl, and substituted heterocycloalkyl.

12. The compound according to claim 11, $R_1$ being selected from —H, —OH, —$NH_2$, —$NO_2$, —Ac, —CN, —NHAc, and —CF$_3$.

13. The compound according to claim 11, $R_2$ being H or an ethyl group.

14. The compound according to claim 11, $R_4$ being selected from H, —OH, —$NH_2$, —$NO_2$, —CF$_3$, fluorine, chloride, bromine, and iodine.

15. The compound according to claim 11, which has antibacterial activity against a bacterial pathogen, wherein the bacterial pathogen is *M. tuberculosis* or non-*tuberculosis* mycobacteria (NTM).

* * * * *